US009896719B2

(12) United States Patent
Piepenburg et al.

(10) Patent No.: US 9,896,719 B2
(45) Date of Patent: *Feb. 20, 2018

(54) DNA GLYCOSYLASE/LYASE AND AP ENDONUCLEASE SUBSTRATES

(71) Applicant: Alere San Diego Inc., San Diego, CA (US)

(72) Inventors: Olaf Piepenburg, Essex (GB); Niall A. Armes, Suffolk (GB)

(73) Assignee: Alere San Diego Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/284,065

(22) Filed: Oct. 3, 2016

(65) Prior Publication Data

US 2017/0175173 A1 Jun. 22, 2017

Related U.S. Application Data

(63) Continuation of application No. 12/800,633, filed on May 18, 2010, now Pat. No. 9,469,867.

(60) Provisional application No. 61/179,793, filed on May 20, 2009.

(51) Int. Cl.
  *C12Q 1/6816* (2018.01)
  *C12Q 1/68* (2018.01)
  *C07H 21/00* (2006.01)

(52) U.S. Cl.
  CPC .......... *C12Q 1/6816* (2013.01); *C07H 21/00* (2013.01); *C12Q 2521/301* (2013.01); *C12Q 2521/531* (2013.01); *C12Q 2525/119* (2013.01)

(58) Field of Classification Search
  None
  See application file for complete search history.

(56) References Cited

U.S. PATENT DOCUMENTS

| 4,683,195 A | 7/1987 | Mullis et al. |
| 4,965,188 A | 10/1990 | Mullis et al. |
| 5,223,414 A | 6/1993 | Zarling et al. |
| 5,273,881 A | 12/1993 | Sena et al. |
| 5,326,692 A | 7/1994 | Brinkley et al. |
| 5,354,668 A | 10/1994 | Auerbach |
| 5,418,149 A | 5/1995 | Gelfand et al. |

(Continued)

FOREIGN PATENT DOCUMENTS

| CA | 2444649 | 10/2002 |
| CA | 2476481 | 9/2003 |

(Continued)

OTHER PUBLICATIONS

Office Action in corresponding European Application No. 10180482.1, dated Jan. 17, 2017, pp. 1-7.

(Continued)

*Primary Examiner* — Robert T. Crow
(74) *Attorney, Agent, or Firm* — Andrew Gill; Belinda Lew

(57) ABSTRACT

A new class of nucleic acid substrates for AP endonucleases and members of the glycosylase/lyase family of enzymes is described. Representatives of each family, the enzymes Nfo and fpg, respectively, cleave nucleic acid backbones at positions in which a base has been replaced by a linker to which a variety of label moieties may be attached. The use of these synthetic substrates embedded within oligonucleotides is of utility in a number of applications.

16 Claims, 6 Drawing Sheets

Comparison of natural abasic sites, tetrahydrofuran, and dR-O- [C]n structures

(56) References Cited

U.S. PATENT DOCUMENTS

| | | | |
|---|---|---|---|
| 5,430,136 A * | 7/1995 | Urdea | C07F 9/10 536/24.3 |
| 5,455,166 A | 10/1995 | Walker | |
| 5,536,649 A | 7/1996 | Fraiser et al. | |
| 5,556,751 A | 9/1996 | Stefano | |
| 5,591,609 A | 1/1997 | Auerbach | |
| 5,614,389 A | 3/1997 | Auerbach | |
| 5,635,347 A | 6/1997 | Link et al. | |
| 5,656,430 A | 8/1997 | Chirikjian | |
| 5,665,572 A | 9/1997 | Ikeda et al. | |
| 5,670,316 A | 9/1997 | Sena et al. | |
| 5,705,366 A | 1/1998 | Backus | |
| 5,712,124 A | 1/1998 | Walker | |
| 5,731,150 A | 3/1998 | Sandhu et al. | |
| 5,733,733 A | 3/1998 | Auerbach | |
| 5,744,311 A | 4/1998 | Fraiser et al. | |
| 5,792,607 A | 8/1998 | Backman et al. | |
| 5,834,202 A | 11/1998 | Auerbach | |
| 5,849,547 A | 12/1998 | Cleuziat | |
| 5,858,652 A | 1/1999 | Laffler et al. | |
| 5,916,779 A | 6/1999 | Pearson et al. | |
| 5,942,391 A | 8/1999 | Zhang et al. | |
| 6,087,112 A | 7/2000 | Dale | |
| 6,140,054 A | 10/2000 | Wittwer et al. | |
| 6,165,793 A | 12/2000 | Stemmer | |
| 6,251,600 B1 | 6/2001 | Winger et al. | |
| 6,379,899 B1 | 4/2002 | Ullman | |
| 6,387,621 B1 | 5/2002 | Wittwer | |
| 6,448,065 B2 | 9/2002 | Laugharn, Jr. et al. | |
| 6,509,157 B1 | 1/2003 | Martinez | |
| 6,566,103 B2 | 5/2003 | Wijnhoven et al. | |
| 6,699,693 B1 | 3/2004 | Marians et al. | |
| 6,929,915 B2 | 8/2005 | Benkovic et al. | |
| 7,112,423 B2 | 9/2006 | Van Ness et al. | |
| 7,252,940 B2 | 8/2007 | Kutyavin et al. | |
| 7,270,981 B2 | 9/2007 | Armes et al. | |
| 7,282,328 B2 | 10/2007 | Kong | |
| 7,399,590 B2 | 7/2008 | Piepenburg et al. | |
| 7,435,561 B2 | 10/2008 | Piepenburg et al. | |
| 7,485,428 B2 | 2/2009 | Armes et al. | |
| 7,666,598 B2 | 2/2010 | Piepenburg et al. | |
| 7,763,427 B2 | 7/2010 | Piepenburg et al. | |
| 7,777,958 B2 | 8/2010 | Shimmo et al. | |
| 8,017,339 B2 | 9/2011 | Piepenburg et al. | |
| 8,030,000 B2 | 10/2011 | Piepenburg et al. | |
| 8,062,850 B2 | 11/2011 | Piepenburg et al. | |
| 8,071,308 B2 | 12/2011 | Piepenburg et al. | |
| 8,426,134 B2 | 4/2013 | Piepenburg et al. | |
| 8,431,347 B2 | 4/2013 | Millar et al. | |
| 8,574,846 B2 | 11/2013 | Piepenburg et al. | |
| 8,945,845 B2 | 2/2015 | Piepenburg et al. | |
| 8,962,255 B2 | 2/2015 | Piepenburg et al. | |
| 9,469,867 B2 * | 10/2016 | Piepenburg | C12Q 1/6816 |
| 2001/0044111 A1 | 11/2001 | Carr et al. | |
| 2002/0061530 A1 | 5/2002 | Belotserkovskii et al. | |
| 2002/0155573 A1 | 10/2002 | Lanes et al. | |
| 2003/0082565 A1 * | 5/2003 | Jang | C12N 15/1013 435/6.13 |
| 2003/0082590 A1 | 5/2003 | Van Ness et al. | |
| 2003/0108936 A1 | 6/2003 | Wagner | |
| 2003/0138800 A1 | 7/2003 | Van Ness et al. | |
| 2003/0143525 A1 | 7/2003 | Benkovic et al. | |
| 2003/0219792 A1 | 11/2003 | Armes et al. | |
| 2003/0228611 A1 | 12/2003 | Chruch et al. | |
| 2004/0038213 A1 | 2/2004 | Kwon | |
| 2004/0058378 A1 | 3/2004 | Kong et al. | |
| 2004/0091864 A1 | 5/2004 | French et al. | |
| 2004/0101893 A1 | 5/2004 | Kutyavin et al. | |
| 2004/0137456 A1 | 7/2004 | Yokota et al. | |
| 2004/0224336 A1 | 11/2004 | Wagner | |
| 2005/0003395 A1 * | 1/2005 | Gellibolian | C12Q 1/6837 506/12 |
| 2005/0059003 A1 | 3/2005 | Enoki et al. | |
| 2005/0112631 A1 | 5/2005 | Piepenburg et al. | |
| 2005/0136443 A1 | 6/2005 | Shigemori | |
| 2006/0110765 A1 | 5/2006 | Wang | |
| 2006/0154286 A1 | 7/2006 | Kong et al. | |
| 2007/0031869 A1 | 2/2007 | McCoy et al. | |
| 2007/0042427 A1 | 2/2007 | Gerdes et al. | |
| 2007/0054296 A1 | 3/2007 | Piepenburg et al. | |
| 2007/0154914 A1 | 7/2007 | Gelfand et al. | |
| 2007/0259348 A1 | 11/2007 | Phadke et al. | |
| 2008/0076160 A1 | 3/2008 | Armes et al. | |
| 2008/0293045 A1 | 11/2008 | Piepenburg et al. | |
| 2009/0017453 A1 | 1/2009 | Maples et al. | |
| 2009/0017462 A1 | 1/2009 | Piepenburg et al. | |
| 2009/0029421 A1 | 1/2009 | Piepenburg et al. | |
| 2009/0081670 A1 | 3/2009 | Maples et al. | |
| 2009/0269813 A1 | 10/2009 | Piepenburg et al. | |
| 2009/0325165 A1 | 12/2009 | Armes et al. | |
| 2010/0234245 A1 | 9/2010 | McGee et al. | |
| 2010/0311127 A1 | 12/2010 | Piepenburg et al. | |
| 2011/0053153 A1 | 3/2011 | Piepenburg et al. | |
| 2011/0059506 A1 | 3/2011 | Piepenburg et al. | |
| 2011/0065106 A1 | 3/2011 | Armes et al. | |
| 2012/0015367 A1 | 1/2012 | Piepenburg et al. | |
| 2012/0021462 A1 | 1/2012 | Armes et al. | |
| 2012/0058517 A1 | 3/2012 | Piepenburg et al. | |
| 2012/0082990 A1 | 4/2012 | Piepenburg et al. | |
| 2012/0129173 A1 | 5/2012 | Piepenburg et al. | |
| 2014/0099674 A1 | 4/2014 | Piepenburg et al. | |
| 2014/0141434 A1 | 5/2014 | Armes et al. | |
| 2014/0234846 A1 | 8/2014 | Piepenburg et al. | |
| 2014/0295436 A1 | 10/2014 | Piepenburg et al. | |

FOREIGN PATENT DOCUMENTS

| | | |
|---|---|---|
| EP | 0 624 643 | 4/1994 |
| EP | 0 702 090 | 3/1996 |
| EP | 0 810 436 | 12/1997 |
| EP | 1403379 | 3/2004 |
| EP | 1 420 069 | 5/2004 |
| EP | 1 564 306 | 8/2005 |
| JP | 08-103300 | 4/1996 |
| JP | 2000-500981 | 2/2000 |
| JP | 2002-512044 | 4/2002 |
| JP | 2003 -38180 | 7/2003 |
| JP | 2004-512843 | 4/2004 |
| JP | 2005-518215 | 6/2006 |
| JP | 2008-515447 | 5/2008 |
| JP | 2009-502161 | 1/2009 |
| JP | 2011-505127 | 2/2011 |
| WO | WO 91/17267 | 11/1991 |
| WO | WO 93/05178 | 3/1993 |
| WO | WO 97/20078 | 6/1997 |
| WO | WO 98/08975 | 3/1998 |
| WO | WO99/60158 | 11/1999 |
| WO | WO 99/60158 | 11/1999 |
| WO | WO 00/41524 | 7/2000 |
| WO | WO 00/46408 | 8/2000 |
| WO | WO 02/086167 | 10/2002 |
| WO | WO 03/027640 | 4/2003 |
| WO | WO 03/038053 | 5/2003 |
| WO | WO 03/072805 | 9/2003 |
| WO | WO 04/007078 | 1/2004 |
| WO | WO 04/027025 | 4/2004 |
| WO | WO 04/090169 | 10/2004 |
| WO | WO 05/118853 | 12/2005 |
| WO | WO06/040187 | 4/2006 |
| WO | WO 06/040187 | 4/2006 |
| WO | WO 07/096702 | 8/2007 |
| WO | WO2010141940 | 12/2010 |
| WO | WO 2013185081 | 12/2013 |

OTHER PUBLICATIONS

Cai, "An Inexpensive and Simple Nucleic Acid Dipstick for Rapid Pathogen Detection," LAUR #05-9067 of Los Alamos National Laboratory, Aug. 22, 2006.

Kool, "Replacing the Nucleobases in DNA with Designer Molecules," Acc. Chem. Res., 35:936-943, 2002.

(56) References Cited

OTHER PUBLICATIONS

Raap et al., "Synthesis and Proton-NMR Studies of Oligonucleotides Containing and Apurinic (AP) Site," J. Biom. Structure & Dynamics, 5(2):219-247, 1987.
Saiki et al., "Primer-Directed Enzymatic Amplification of DNA with a Thermostable DNA Polymerase," Science, 239:487-491, 1988.
Takeshita et al., "Oligodeoxynucleotides Containing Synthetic Abasic Sites," J. Bio. Chem., 262(21):10171-10179, 1987.
Van Ness et al., "Isothermal reactions for the amplification of oligonucleotides," Proc. Nat. Acad. Sci. USA, 100(8):4504-4509, 2003.
The International Search Report, for the corresponding PCT Application No. PCT/US2010/035232, dated Sep. 28, 2010.
The International Preliminary Report on Patentability, PCT Application No. PCT/US2010/035232, dated Dec. 1, 2011.
Accession: NP_861734 [GI: 32453528], Definition: UvsX RecA-like recombination protein [Enterobacteria phage RB69]. NCBI Sequence Revision History [online]; Mar. 30, 2006 uploaded, NCBI, <URL: http://www.ncbi.nlm.nih.gov/protein/32453528?sat=12&satkey=7706006> [retrieved on Aug. 30, 2011].
Accession: NP_861890 [GI: 32453681], Definition: UvsY recombination, repair and ssDNA binding protein [Enterobacteria phage RB69]. NCBI Sequence Revision History [online]; Mar. 30, 2006 uploaded, NCBI, <URL: http://www.ncbi.nlm.nih.gov/protein/32453681?sat=12&satkey=7706006> [retrieved on Aug. 30, 2011].
Adams et al., "Dissociation of RecA filaments from duplex DNA by the RuvA and RuvB DNA repair proteins," Proc. Natl. Acad. Sci. USA 91:9901-9905, 1994.
Alexseyev et al., "Genetic Characteristics of New recA Mutants of *Escherichia coli* K-12," J. Bacteriol., 178:2018-2024, 1996.
Amasino, "Acceleration of Nucleic Acid Hybridization Rate by Polyethylene Glycol," Anal. Biochem., 152:304-307, 1986.
Bains and Smith, "A Novel Method for Nucleic Acid Sequence Determination," J. Theor. Biol., 135:303-307, 1988.
Bar-Ziv and Libchaber, "Effects of DNA sequence and structure on binding of RecA to single-stranded DNA," PNAS USA, 98(16):9068-9073.
Baumann et al., "Purification of human Rad51 protein by selective spermidine precipitation," Mutat. Res., 384:65-72, 1997.
Benedict and Kowalczykowski, "Increase of the DNA Strand Assimiliation Activity of recA Protein by Removal of the C Terminus and Structure-Function Studies of the Resulting Protein Fragment," J. Biol. Chem., 263(30):15513-15520, 1988.
Benkovic et al., "Replisome-Mediated DNA Replication," Annu. Rev. Biochem., 70:181-208, 2001.
Bennett and Holloman, "A RecA Homologue in Ustilago maydis That Is Distinct and Evolutionarily Distant from Rad51 Actively Promotes DNA Pairing Reactions in the Absence of Auxiliaiy Factors," Biochemistry, 40:2942-2953, 2001.
Better and Helinski, "Isolation and Characterization of the recA Gene of Rhizobium meliloti," J. Bacteriol, 155:311-316, 1983.
Bianco and Weinstock, "Interaction of the RecA protein of *Escherichia coli* with single-stranded oligodeoxyribonucleotides," Nucleic Acids Research, 24(24):4933-4939, 1996.
Bianco et al., "DNA Strand Exchange Proteins: A Biochemical and Physical Comparison," Frontiers in Bioscience, 3:D570-D603, 1998.
Borjac-Natour et al., "Divergence of the mRNA targets for the Ssb proteins of bacteriophages T4 and RB69," Virology J., 1(4):1-14, 2004.
Bork et al., "The RecOR proteins modulate RecA protein function at 5' ends of single-stranded DNA," EMBO J., 20:7313-7322, 2001.
Bork et al., "RecA Protein Filaments Disassemble in the 5' to 3' Direction on Single-stranded DNA," J. Biol. Chem., 276:45740-45743, 2001.
Butler et al., "Investigating Structural Changes Induced by nucleotide Binding to RecA Using Difference FTIR," Biophysical J., 82(4):2198-2210, 2002.

Byrd and Raney, "Protein displacement by an assembly of helicase molecules aligned along single-stranded DNA," Nat. Struct. Mol. Biol., 11(6):531-538, 2004.
Chan et al., "Effects of Polyethylene Glycol on Reverse Transcriptase and Other polymerase Activities," Biochim. Biophys. Acta., 606(2):353-361, 1980.
Compton, "Nucleic acid sequence-based amplification," Nature, 350:91-92, 1991.
Conklin and Drake, "Isolation and Characterization of conditional Alleles of bacteriophage T4 Genes *uvsX* and *uvsY*," Genetics, 107:505-523, 1984.
Cox et al., "The importance of repairing stalled replication forks," Nature, 404:37-41, 2000.
Cox et al., "A Simple and Rapid Procedure for the Large Scale Purification of the recA protein of *Escherichia coli*," J. Biol. Chem., 256:4676-4678, 1981.
Cromie and Leach, "Control of Crossing Over," Mol. Cell., 6:815-826. 2000.
Decker et al., "In Vitro Initiation of DNA Replication in Simian Virus 40 Chromosomes," J. Biol. Chem., 262(22):10863-10872, 1987.
Demidov, "Rolling-circle amplification in DNA diagnostics: the power of simplicity," Expert Rev. Mol. Diagn., 2(6):89-95, 2002.
Digard et al., "The Extreme C Terminus of Herpes Simplex Vitus DNA Polymerase Is Crucial for Functional Interaction with Processivity Factor UL42 and for Viral Replication," J. Virol., 67(1):398-406, 1993.
Dillingham and Kowalczykowski, "A Step Backward in Advancing DNA Replication: Rescue of Stalled Replication Forks by RecG," Mol. Cell., 8:734-736, 2001.
Dong et al., "A coupled complex of T4 DNA replication helicase (gp41) and polymerase (gp43) can perform rapid and processive DNA strand-displacement synthesis," Proc. Natl. Acad. Sci. USA, 93:14456-14461, 1996.
Drmanac, et al., "Sequencing of Megabase Plus DNA by Hybridization: Theory of the Method," Genomics, 4:114-128, 1989.
Edwards et al., "Genetic Variation at Five Trimeric and Tetrameric Tandem Repeat Loci in Four Human Population Groups," Genomics, 12:241-253, 1992.
Eggler et al., "The C Terminus of the *Escherichia coli* RecA Protein Modulates the DNA Binding Competition with Single-stranded DNA-binding Protein," J. Biol. Chem., 278:16389-16396, 2003.
Eggleston and West, "Cleavage of Holliday Junctions by the *Escherichia coli* RuvABC Complex," J. Biol. Chem., 275:26467-26476, 2000.
Elias-Arnanz and Salas, "Bacteriophage ø29 DNA replication arrest caused by codirectional collisions with the transcription machinery," EMBO J., 16:5775-5783, 1997.
Ellis, "Macromolecular crowding: obvious but underappreciated," Trends in Biochem. Sci., 26(10):597-604, 2001.
Ellouze et al., "Evidence for elongation of the helical pitch of the RecA filament upon ATP and ADP binding using small-angle neutron scattering," Eur. J. Biochem., 23392):579-583, 1995.
Enright et al., The evolutionary history of methicillin-resistant *Staphylococcus aureus* (MRSA), Proc. Natl. Acad. Sci. USA, 99:7687-7692, 2002.
Fahy et al., "Self-sustained sequence replication (3SR): an isothermal transcription-based amplification system alternative to PCR," Genome Res, 1:25-33, 1991.
Ferrari et al., "Co-operative Binding of *Escherichia Coli* SSB Tetramers to Single-stranded DNA in the $(SSB)_{35}$ Binding Mode," J. Mol. Biol, 236:106-123, 1994.
Formosa et al., "Affinity purification of bacteriophage T4 proteins essential for DNA replication and genetic recombination," Proc. Natl. Acad. Sci. USA, 80:2442-2446, 1983.
Formosa and Alberts, "Purification and Characterization of the T4 Bacteriophage uvsX Protein," J. Biol. Chem., 261:6107-6118, 1986.
Formosa and Alberts, "DNA Synthesis Dependent on Genetic Recombination: Characterization of a Reaction Catalyzed by Purified Bacteriophage T4 Proteins," Cell, 47:793-806, 1986.
Fu et al., "Dynamics of DNA-tracking by two sliding-clamp proteins," EMBO J., 15(16):4414-4422, 1996.

(56) References Cited

OTHER PUBLICATIONS

Fuller et al., "Enzymatic replication of the origin of the *Escherichia coli* chromosome," Proc. Natl. Acad. Sci. USA, 78(12):7370-7374, 1981.

Giedroc et al., "The Function of Zinc in Gene 32 Protein from T4," Biochem., 26:5251-5259, 1987.

Giedroc et al., "Zn(II) Coordination Domain Mutants of T4 Gene 32 protein," Biochem., 31:765-774, 1992.

Ginocchio, "Life Beyond PCR: Alternative Target Amplification Technologies for the Diagnosis of Infectious Diseases, Part II," Clin. Microbiol. Newsletter, 26(17):129-136, 2004.

Glover and McHenry, "The DNA Polymerase III Holoenzyme: An Asymmetric Dimeric Replicative Complex with Leading and Lagging Strand Polymerases," Cell., 105:925-934.

Goodman et al., "Cloning and expression in *Escherichia coli* of a recA-like gene from *Bacteroides fragilis*," Gene, 58:265-271, 1987.

Hacker and Alberts, "Overexpression, Purification, Sequence Analysis, and Characterization of the T4 Bacteriophage dda DNA Helicase," J. Biol. Chem., 267:20674-20681, 1992.

Hammond et al., "Evaluation of 13 Short Tandem Repeat Loci for Use in Personal Identification Applications," Am. J. Hum. Genetics, 55:175-189, 1994.

Harris and Griffith, "UvsY Protein of Bacteriophage T4 is an Accessory Protein for in Vitro Catalysis of Strand Exchange," J. Mol. Biol., 206:19-27, 1989.

Han-is and Griffith, "Visualization of the Homologous Pairing of DNA Catalyzed by the Bacteriophage T4 UvsX Protein," J. Biol. Chem., 262:9285-9292, 1987.

Harris and Griffith, "Formation of D Loops by the UvsX Protein of T4 Bacteriophage: A Comparison of the Reaction Catalyzed in the Presence or Absence of Gene 32 Protein," Biochem., 27:6954-6959, 1988.

Harvey et al., "Characterization and applications of CataCleave probe in real-time detection assays," Anal. Biochem., 333(2):246-255, 2004.

Heid et al., "Real time quantitative PCR," Genome Res., 6(10):986-994, 1996.

Heyer and Kolodner, "Purification and Characteirzation of a Protein from *Saccharomyces cerevisiae* That Binds Tightly to Single-Stranded DNA and Stimulates a cognate Strand Exchange Protein," Biochem. 28:2856-2862, 1989.

Hickson et al., "A Temperature Sensitive RecA Protein of *Escherichia coli*," Mol. Gen. Genet., 184:68-72, 1981.

Hopp et al., "A Short Polypeptide Marker Sequence Useful for Recombinant Protein Identification and Purification," Biotech., 6:1204-1210, 1988.

Hsieh et al., "The synapsis event in the homologous pairing of DNAs: RecA recognizes and pairs less than one helical repeat of DNA," Proc. Natl. Acad. Sci. USA, 89:6492-6496, 1992.

Huang et al., "Relationship between Bacteriophage T4 and T6 DNA Topoisomerases," J. Biol. Chem., 260(15):8973-8977, 1985.

Huletsky et al., "New Real-Time PCR Assay for Rapid Detection of Methicillin-Resistant *Staphylococcus aureus* Directly from Specimens Containing a Mixturre of Staphylococci," J. Clin. Microbiol., 42:1875-1884, 2004.

Ischenko and Saparbaev, "Alternative nucleotide incision repair pathway for oxidative DNA damage," Nature, 415(6868):183-187, 2002.

Ishmael et al., "Protein-Protein Interactions in the Bacteriophage T4 Replisome," J. Biol. Chem., 278(5):3145-3152, 2003.

Jarvis et al., "'Macromolecular Crowding': Thermodynamic Consequences for Protein-Protein Interactions with in the T4 DNA Replication Complex," J. Biol. Chem., 265(25):15160-15167, 1990.

Kaboord and Benkovic, "Rapid assembly of the bacteriophage T4 core replication complex on a linear primer/template construct," Proc. Natl. Acad. Sci. USA, 90:10881-10885, 1993.

Kaiser et al., "A Comparison of Eubacterial and Archaeal Structure-specific 5'-Exonucleases," J. Biol. Chem., 274(30):21387-21394, 1999.

Kato and Kuramitsu, "RecA Protein from an Extremely Thermophilic Bacterium, *Thermus thermophiles* HB8," J. Biochem., 114:926-929, 1993.

Katz and Bryant, "Interdependence of the Kinetics of NTP Hydrolysis and the Stability of the RecA-ssDNA Complex," Biochem., 40:11082-11089, 2001.

Kelman and O'Donnell, "DNA Polymerase III Holoenzyme: Structure and Function of a Chromosomal Replicating Machine," Annu. Rev. Biochem., 64:171-2000.

Khrapko et al., "An oligonucleotide hybridization approach to DNA sequencing," FEBS Lett., 256:118-122, 1989.

Komori et al., "Both RadA and RadB Are Involved in Homologous Recombination in *Pyrococcus furiosus*," J. Biol. Chem., 275:33782-33790, 2000.

Kowalczykowski et al., "Effects of the *Escherichia coli* SSB Protein on the Binding of *Escherichia coli* RecA Protein to Single-stranded DNA—Demonstration of Competitive Binding and the Lack of a Specific Protein-Protein Interaction," J. Mol. Biol., 193:81-95, 1987.

Kreader, "Relief of amplification inhibition in PCR with bovine serum albumin or T4 gene 32 protein," Appl. Env. Microbiol., 62:1102-1106, 1996.

Kuil et al., "The internal dynamics of gene 32 protein-DNA complexes studied by quasi-elastic light scattering," Biophys. Chem., 32:211-227, 1988.

Kuil et al., "A Refined Calculation of the Solution Dimensions of the Complex Between gene 32 Protein and Single Stranded DNA Based on Estimates of the Bending Persistence Length," J. Biomol. Struct. Dyn. 7(4):943-957, 1990.

Kuramitsu et al., "A Large-Scale Preparation and Some Physicochemical Properties of RecA Protein," J. Biochem., 90:1033-1045, 1981.

Kurumizaka et al., "A Chimeric RecA Protein Exhibits Altered Double-stranded DNA Binding," J. Biol. Chem., 269:3068-3075, 1994.

Lavery and Kowalczykowski, "Enhancement of recA Protein-promoted DNA Strand Exchange Activity by Volume-occupying Agents," J. Biol. Chem., 267:9301-9314, 1992.

Lavery and Kowalczykowski, "A Postsynaptic Role for Single-stranded DNA-binding Protein in recA Protein-promoted DNA Strand Exchange," J. Biol. Chem., 267(13):9315-9320, 1992.

LeBowitz and McMacken, "The bacteriophage λ and P protein initiators promote the replication of single-stranded DNA," 12(7):1-20, 1984.

Lerman, "A Transition to a Compact Form of DNA in Polymer Solutions," Proc. Nat. Acad. Sci. USA, 68(8):1886-1890, 1971.

Levin et al., "Homogeneous *Escherichia coli* Endonuclease IV," J. Biol. Chem., 263:8066-8071, 1988.

Liu et al., "The Ordered Assembly of the ØX174-type Primosome," J. Biol. Chem., 271:15656-15661, 1996.

Lohman and Ferrari, "*Escherichia coli* Single-Stranded DNA-Binding Protein: Multiple DNA-Binding Modes and Cooperativities," Annu. Rev. Biochem., 63:527-570, 1994.

Lovett and Roberts, "Purification of a RecA Protein Analogue from *Bacillus subtilis*," J. Biol. Chem., 260:3305-3313, 1985.

Lusetti et al., "Magnesium Ion-dependent Activation of the RecA Protein Involves the C Terminus," J. Biol. Chem., 278(18):16381-16388, 2003.

Lutz-Freyermuth et al., "Quantitative determination that one of two potential RNA-binding domains of the a protein component of the U1 small nuclear ribonucleoprotein complex binds with high affinity to stem-loop II of UI RNA," Proc. Natl. Acad. Sci. USA, 87:6393-6397, 1990.

Lysov et al., "Establishing Nucleotide Sequence of DNA using Oligonucleotide Hybridization. Novel Method," SSSR 303:1508-1511, 1988 (English translation).

Maeshima et al., "Purification and characterization of XRad51.1 protein, Xenopus RAD51 homologue: recombinant XRad51.1 promotes strand exchange reaction," Genes Cells, 1:1057-1068, 1996.

Maki et al., "DNA Polymerase III Holoenzyme of *Escherichia coli*," J. Biol. Chem., 263(14):6570-6578, 1988.

Malkov and Camerini-Otero, Photocross-links between Single-stranded DNA and *Escherichia coli* RecA Protein Map to Loops L1

(56) References Cited

OTHER PUBLICATIONS (Amino Acid Residues 157-164) and L2 (Amino Acid Residues 195-209),: J. Biol. Chem., 270(50):30230-30233, 1995.
Marians, "Prokaryotic DNA Replication," Annu. Rev. Biochem., 61:673-719, 1992.
Marians, "PriA: At the Crossroads of DNA Replication and Recombination," Prog. Nucleic Acid Res. Mol. Biol., 63:39-67, 1999.
Marras et al., "Multiplex detection of single-nucleotide variations using molecular beacons," Genet. Anal. Biomolec. Eng., 14:151-156, 1999.
Martin et al., "GAP Domains Responsible for Ras p21-Dependent Inhibition of Muscarinic Atrial $K^+$ Channel Currents," Science, 255:192-194, 1992.
Maxam and Gilbert, "A new method for sequencing DNA," Proc. Natl. Acad. Sci. USA, 74:560-564, 1877.
Mazin and Kowalczykowski, "The function of the secondary DNA-binding site of RecA protein during DNA strand exchange," Proc. Natl. Acad. Sci. USA, 74:560-564, 1977.
McGlynn and Lloyd, "RecG helicase activity at three- and four-strand DNA structures," Nucl. Acid Res., 27:3049-3056, 1999.
McGlynn et al., "Characterisation of the catalytically active form of RecG helicase," Nucl. Acid Res., 28:2324-2332, 2000.
Minton, "The Influence of Macromolecular Crowding and Macromolecular Confinement on Biochemical Reactions in Physiological Media," J. Biol. Chem., 276(14):10577-10580, 2001.
Mitra and Church, "In situ localized amplification and contact replication of many individual DNA molecules," Nucl. Acids Res., 27(24):e34i-e34vi.
Mizuuchi, "In Vitro Transposition of Bacteriophage Mu: A Biochemical Approach to a Novel Replication Reaction," Cell, 35:785-794, 1983.
Morel et al., "Recombination-dependent Repair of DNA Double-strand Breaks with Purified Proteins from *Escherichia coli*," J. Biol. Chem., 272:17091-17096, 1997.
Morrical et al., "Amplification of Snap-back DNA Synthesis Reactions by the uvsX Recombinase of Bacteriophage T4," J. Biol. Chem., 266:14031-14038, 1991.
Morrical and Alberts, "The UvsY Protein of Bacteriophage T4 Modulates Recombination-dependent DNA Synthesis in Vitro," J. Biol. Chem., 265:15096-15103, 1990.
Morris and Raney, "DNA Helicases Displace Streptavidin from Biotin-Labeled Oligonucleotides," Biochem., 38(16):5164-5171, 1999.
Morrison et al., "Quantificationo f Low-Copy Transcripts by Continuous SYBR Green I Monitoring during Amplification," BioTechniques, 24:954-962, 1998.
Mosig et al., "Two recombination-dependent DNA replication pathways of bacteriophage T4, and their roles in mutagenesis and horizontal gene transfer," Proc. Natl. Acad. Sci. USA, 98:8306-8311, 2011.
Nadler et al., "A Novel Function for Zinc(II) in a Nucleic Acid-binding Protein," J. Biol. Chem., 265(18):10389-10394, 1990.
Nadeau et al., "Real-Time, Sequence-Specific Detection of Nucleic Acids during Strand Displacement Amplification," Anal. Biochem., 276(2):177-187, 1999.
Nagai et al., "Additive Effects of Bovine Serum Albumin, Dithiothreitol, and Glycerol in PCR," 44:157-163, 1998.
Naimushin et al., "Effect of Polyethylene Glycol on the Supercoiling Free Energy of DNA," Biopolymers, 58(2):204-217, 2001.
Ng and Marians, "The Ordered Assembly of the øX174-type Primosome," J. Biol. Chem., 271:15642-15648, 1996.
Ng and Marians, "The Ordered Assembly of the øX174-type Primosome," J. Biol. Chem., 271:15649-15655, 1996.
Okazaki and Kornberg, "Enzymatic Synthesis of Deoxyribonucleic Acid," J. Biol. Chem., 239:259-268, 1964.
Paulus and Bryant, "Time-Dependent Inhibition of recA Protein-Catalyzed ATPHydrolysis by ATPγS: Evidence for a Rate-Determining Isomerization of the recA-ssDNA Complex," Biochem., 36:7832-7838, 1997.

Petrov et al., "Plasticity of the Gene Functions for DNA Replication in the T4-like Phages," J. Mol. Biol., 361:46-68, 2006.
Pevzner, "1-Tuple DNA Sequencing: Computer Analysis," J. Biomol. Struct. Dyn., 7:63-73, 1989.
Pham et al., "A model for SOS-lesion-targeted mutations in *Escherichia coli*," Nature, 409:366-370, 2001.
Piepenburg et al., "DNA Detection Using Recombination Proteins," PLOS Biology, 4(7):1115-1121, 2006.
Pierre and Paoletti, "Purification and Characterization of recA Protein from *Salmonella typhimurium*," J. Biol. Chem., 258:2870-2874, 1983.
Podust et al., "Replication Factor C Disengages from Proliferating Cell Nuclear Antigen (PCNA) upon Sliding Clamp Formation, and PCNA Itself Tethers DNA Polymerase δ to DNA," J. Biol. Chem., 273(48):31992-31999, 1998.
Pomp and Medrano, "Organic Solvents as Facilitators of Polymerase chain Reaction," Biotechniques, 10(1):58-59, 1991.
Qiu and Giedroc, "Effects of Substitution of Proposed Zn(II) Ligand $His^{81}$ or $His^{64}$ in Phage T4 Gene 32 Protein: Spectroscopic Evidence for a Novel Zinc Coordination Complex," Biochem., 33(26):8139-8148, 1994.
Raap, "Advances in fluorescence in situ hybridization," Mutation Research, 400:287-298, 1998.
Rashid et al., "RecA/Rad51 Homolog from *Thermococcus kodakaraensis* KOD1," Methods Enzymol., 334:261-270, 2001.
Reddy et al., "Assembly of a functional replication complex without ATP hydrolysis: A direct interaction of bacteriophage T4 gp45 with T4 DNA polymerase," Proc. Natl. Acad. Sci. USA, 90:3211-3215, 1993.
Reddy et al., "Using Macromolecular Crowding Agents to Identify Weak Interactions within DNA Replication Complexes," Methods Enzymol., 262:466-476, 1995.
Riddles and Lehman, "The Formation of Plectonemic Joints by the recA Protein of *Escherichia coli*," J. Biol. Chem., 260:170-173, 1985.
Rivas et al., "Life in a crowded world—Workshop on the Biological Implications of Macromolecular Crowding," EMBO Reports, 5(1):23-27, 2004.
Ronaghi et al., "A Sequencing Method Based on Real-Time Pyrophosphate," Science, 281:363-365, 1998.
Rosselli and Stasiak, "Energetics of RecA-mediated Recombination Reactions Without ATP Hydrolysis RecA Can Mediate Polar Strand Exchange But Is Unable to Recycle," J. Mol. Biol., 216:335-352, 1990.
Roux, "Optimization and troubleshooting in PCR," Genome Res., 4:S185-S194, 1995.
Salinas et al., "Homology Dependence of UvsX Protein-catalyzed Joint Molecule Formation," J. Biol. Chem., 270:5181-5186.
Salinas and Benkovic, "Characterization of bacteriophage T4-coordinated leading- and lagging-strand synthesis on a minicircle substrate," PNAS, 97(13):7196-7201, 2000.
Sanders et al., "Use of a macromolecular crowding agent to dissect interactions and define functions in transcriptional activation by a DNA-tracking protein: Bacteriphage T4 gene 45 protein and late transcription," Proc. Natl. Acad. Sci. USA, 91:7703-7707, 1994.
Sanders et al., "Dual targets of a transcriptional activator that tracks on DNA," EMBO J., 16(11):3124-3132, 1997.
Sanger et al., "DNA sequencing with chain-terminating inhibitors," Proc. Natl. Acad. Sci. USA, 75:5463-5467, 1977.
Sawa and Pearl, "Cloning and Expression of the Uracil-DNA Glycosylase Inhibitor (UGI) From Bacteriophage PBS-1 and Crystallization of a Uracil-DNA Glycosylase-UGI Complex," Proteins, 22(3):287-289, 1995.
Scheerhagen et al., "Binding Stoichiometry of the Gene 32 Protein of Phage T4 in the Complex with Single Stranded DNA Deduced from Boundary Sedimentation," J. Biomol. Struct. Dyn., 3:887-898, 1986.
Scheerhagen et al., "Hydrodynamic studies of a DNA-protein complex—Dimensions of the complex of single-stranded 145 base DNA with gene 32 protein of phage T4 deduced from quasi-elastic light scattering," FEBS Lett., 184(2):221-225, 1985.

(56) References Cited

OTHER PUBLICATIONS

Shan et al., "RecA Protein Filaments: End-dependent Dissociation from ssDNA and Stabilization by RecO and RecR Proteins," J. Mol. Biol., 265:519-540, 1997.
Shibata et al., "Purified *Escherichia coli* recA protein catalyzes homologous pairing of superhelical DNA and single-stranded fragments," Proc. Natl. Acad. Sci. USA, 76:1638-1642, 1979.
Shibata et al., "Homologous pairing in genetic recombination: Formation of D loops by combined action of recA protein and a helix-destabilizing protein," Proc. Natl. Acad. Sci. USA, 77:2606-2610, 1980.
Shibata et al, "Homologous pairing in genetic recombination: Complexes of recA protein and DNA," Proc. Natl. Acad. Sci. USA, 76(10):5100-5104, 1979.
Singleton et al., "Structural Analysis of DNA Replication Fork Reversal by RecG," Cell, 107:79-89, 2001.
Skinner et al., "Use of the Glu-Glu-Phe C-terminal Epitope for Rapid Purification of the Catalytic Domain of Normal and Mutant *ras* GTPase-activating Proteins," J. Biol. Chem., 266:14163-14166, 1991.
Southern et al., "Analyzing and Comparing Nucleic Acid sequences by Hybridization to Arrays of Oligonucleotides: Evaluation Using Experimental Models," Genomics, 13:1008-1017, 1992.
Spies et al., "The RadA protein from a hyperthennophilic archaeon *Pyrobaculum islandicum* is a DNA-dependent ATPase that exhibits two disparate catalytic modes, with a transition temperature at 75° C.," Eur. J. Biochem., 267:1125-1137, 2000.
Steffen and Bryant, "Purification and Characterization of the RecA Protein from *Streptococcus pneumoniae*," Arch. Biochem. Biophys., 382:303-309, 2000.
Story et al., "Structural Relationship of Bacterial RecA Proteins to Recombination Proteins from Bacteriophage T4 and Yeast," Science, 259(5103):1892-1896, 1993.
Sun and Shamoo, "Biochemical characterization of Interactions between DNA Polymerase and Single-stranded DNA-binding Protein in Bacteriophage RB69," J. Biol. Chem., 278(6):3876-3881.
Tang et al., "Roles of *E. coli*DNA polymerases IV and V in lesion-targeted and untargeted SOS mutagenesis," Nature, 404:1014-1018, 2000.
Tinker-Kulberg et al., "A direct interaction between a DNA-tracking protein and a promoter recognition protein: implications for searching DNA sequence," EMBO J., 15(18):5032-5039, 1996.
Tissier et al., "Purification and Characterization of a DNA Strand Transferase from Broccoli," Plant Physiol., 108:379-386, 1995.
Tracy and Kowalczykowski, "In vitro selection of preferred DNA pairing sequences by the *Escherichia coli* RecA protein," Genes Dev., 10:1890-1903, 1996.
Tsurimoto and Matsubara, "Replication of λ dv plasmid in vitro promoted by purified λ O and P proteins," Proc. Natl. Acad. Sci. USA, 79:7639-7643, 1982.
Tyagi et al., "Multicolor molecular beacons for allele discrimination," Nature Biotechnol., 16:49-53, 1998.
Villemain et al., "Mutations in the N-terminal Cooperativity Domain of Gene 32 protein Alter Properties of the T4 DNA Replication and Recombination Systems," J. Biol. Chem., 275:31496-31504, 2000.
Vincent et al., "Helicase-dependent isothermal DNA amplification," EMBO Rep., 5:795-800, 2004.
Volodin and Camerini-Otero, "Influence of DNA Sequence on the Positioning of RecA Monomers in RecA-DNA Cofilaments," J. Biol. Chem., 277(2):1614-1618, 2002.
Volodin et al., "Phasing of RecA monomers on quasi-random DNA sequences," FEBS Letters, 546:203-208, 2003.
Voloshin et al., "Homologous DNA Pairing Promoted by a 20-Amino Acid Peptide Derived from RecA," Science, 272:868-872, 1996.
Voloshin et al., "The Homologous Pairing Domain of RecA also Mediates the Allosteric Regulation of DNA Binding and ATP Hydrolysis: A Remarkable Concentration of Functional Residues," J. Mol. Biol., 303(5):709-720, 2000.
Waidner, et al., "Domain effects on the DNA-interactive properties of bacteriophage T4 gene 32 protein," J. Biol. Chem., 276:2509-16 (2001).
Walker et al., "Isothermal in vitro amplification of DNA by a restriction enzyme/DNA polymerase system," Proc. Natl. Acad. Sci. USA, 89:392-396, 1992.
Walker, "Empirical aspects of strand displacement amplification," Genome Res., 3:1-6, 1993.
Walker et al., "Distantly related sequences in the α- and β-subunits of ATP synthase, myosin, kinases and other ATP-requiring enzymes and a common nucleotide binding fold," EMBO J., 1:945-951, 1982.
Wang et al., "Modular Organization of T4 DNA Polymerase," J. Biol. Chem., 270(44):26558-26564, 1995.
Wang and Mosbaugh, "Uracil-DNA Glycosylase Inhibitor of Bacteriophage PBS2: Cloning and Effects of Expression of the Inhibitor Gene in *Escherichia coli*," J. Bacteriol., 170(3):1082-1091, 1988.
Webb et al., "An Interaction between the *Escherichia coli* RecF and RecR Proteins Dependent on ATP and Double-stranded DNA," J. Biol. Chem., 270:31397-31404, 1995.
Webb et al., "Recombinational DNA Repair: The RecF and RecR Proteins Limit the Extension of RecA Filaments beyond Single-Strand DNA Gaps," Cell, 91:347-356, 1997.
Webb et al., "ATP Hydrolysis and DNA Binding by the *Escherichia coli* RecF Protein," J. Biol. Chem., 274:15367-15374, 1999.
West et al., "Purification and Properties of the recA Protein of *Proteus mirabilis*," J. Biol. Chem., 258:4648-4654, 1983.
Wetmur et al, "Cloning, Sequencing, and Expression f RecA Proteins from Three Distantly Related Thermophilic Eubacteria," J. Biol. Chem., 269:25928-25935, 1994.
Wittwer et al., "Continuous Fluorescence Monitoring of Rapid Cycle DNA Amplification," Biotechniques, 22(1):130-1, 134-138, 1997.
Xu and Marians, "A Dynamic RecA Filament Permits DNA Polymerase-catalyzed Extension of the Invading Strand in Recombination Intermediates," J. Biol. Chem., 277:14321-14328, 2002.
Yang et al., "Comparison of Bacteriophage T4 and UvsX and Human Rad51 Filaments Suggests that RecA-like Polymers May Have Evolved Independently," J. Mol. Biol., 312(5):999-1009, 2001.
Yeh et al., "Divergence of a DNA Replication Gene Cluster in the T4-Related Bacteriophage RB69," J. Bacteriol., 180(8):2005-2013, 1998.
Yonesaki et al., "Purification and some of the functions of the product of bacteriophage T4 recombination genes, uvsX and uvsY," Eur. J. Biochem., 148:127-134, 1985.
Young et al., "The Kinetic Mechanism of Formation of the Bacteriophage T4 DNA polymerase Sliding Clamp," J. Mol. Biol., 264:440-452, 1996.
Zhang et al., "Ramification Amplification: A Novel Isothermal DNA Amplification Method," Mol. Diagn., 6:141-150, 2001.
Zimmerman and Trach, "Macromolecular crowding extends the range of conditions under which DNA polymerase is functional," Biochim. Biophys. Acta., 949:297-304, 1988.
Zimmerman and Minton, "Macromolecular Crowding: Biochemical, Biophysical, and Physiological Consequences," Annu. Rev. Biophys. Biomol. Struct., 22:27-65, 1993.
Zimmerman and Harrison, "Macromolecular crowding increases binding of DNA polymerase to DNA: An adaptive effect," Proc. Natl. Acad. Sci. USA, 84(7):1871-1875, 1987.
Zinchenko and Yoshikawa, "Na$^+$ Shows a Markedly Higher Potential than K$^+$ in DNA Compaction in a Crowded Environment," Biophysical Journal, 88:4118-4123, 2005.
"UvsX RecA-like recombination protein [Enterobacteria phage RB69]", online NCBI, http://www.ncbi.nlm.nih.gov/protein/32350347?sat=13&satkey=7100722, Apr. 5, 2005 (retrieved on Aug. 22, 2012).
"UvsX [Aeromonas phage Aehl]", online NCBI, http://www.ncbi.nlm.nih.gov/protein/38639939?sat=12&satkey=85157, Mar. 30, 2006 (retrieved on Aug. 22, 2012).
Desplats and Krisch, "The diversity and evolution of the T4-type bacteriophages," Res. Microbiol, 154(4):259-267, 2003.

(56) References Cited

OTHER PUBLICATIONS

Miller et al., "Complete Genome Sequence of the Broad-Host-Range vibriophage KVP40: Comparative Genomics of a T4-Related Bacteriophage," J. Bacteriol., 185(17):5220-5233, 2003.
Kim and Chae, "Optimized protocols for the detection of porcine circovirus 2 DNA from formalin-fixed paraffin-embedded tissues using nested polymerase chain reaction and comparison of nested PCR with in situ hybridization," J. Vir. Methods, 92:105-111, 2001.
Miyamoto et al., "Development of a New Seminested PCR Method for Detection of *Legionella* Species and Its Application to Surveillance of Legionellae in Hospital Cooling Tower Water," Applied and Environmental Microbiology, 63(7):2489-2494, 1997.
Monis and Saint, "Development of a Nested-PCR Assay for the Detection of Cryptosporidium Parvum in Finished Water," Wat. Res., 35(7):1641-1648, 2001.
Ozbas et al., "Development of a multiplex and semi-nested PCR assay for detection of Yersinia enterocolitica and Aeromonas hydrophila in raw milk," Food Microbiology, 17:197-203, 2000.
Barnes and Rowlyk, "Magnesium precipitate hot start method for PCR," Mol. and Cell. Probes, 16(3):167-171, 2002.
Crowe et al., "Is Trehalose Special for Preserving Dry Biomaterials?," Biophys. J., 71(4):2087-2093, 1996.
Mannarelli and Kurtzman, "Rapid Identification of *Candida albicans* and Other Human Pathogenic Yeasts by Using Short Oligonucleotides in a PCR," J. Clin. Microbiol., 36(6):1634-1641, 1998.
Ramos et al., "Stabilization of Enzymes against Thermal Stress and Freeze-Drying by Mannosylglycerate," Appl. And Env. Microbiol., 63(10):4020-4025, 1997.
Office action in corresponding Canadian application 2,476,481, dated May 16, 2013, 9 pages.
Gill et al., "Nucleic acid isothermal amplification technologies: a review," Nucleosides Nucleotides Nucleic Acids 2008 27:224-243.
Mukai et al., "Highly efficient isothermal DNA amplification system using three elements of 5'-DNA-RNA-3' chimeric primers, RNaseH and strand-displacing DNA polymerase," 2007, J. Biochem. 142:273-281.
Tan et al., "Isothermal DNA amplification coupled with DNA nanosphere-based colorimetric detection," Anal. Chem. 2005, 77:7984-7992.
Lizard et al., Nature Biotech. 1998, 6:1197-1202.
Mori et al., "Loop-mediated isothermal amplification (LAMP): a rapid, accurate, and cost-effective diagnostic method for infectious diseases," J. Infect. Chemother. 2009 15:62-69.
Kurn et al., "Novel isothermal, linear nucleic acid amplification systems for highly multiplexed applications," Clin. Chem. 2005, 51:10, 1973-1981.
Piekarowicz et al., "Characterization of the dsDNA prophage sequences in the genome of Neisseria gonorrhoeae and visualization of productive bacteriophage," 2007, BMC Microbiol., 7:66.
Liu et al., 2005, "Rapid identification of *Streptococcus pyogenes* with PCR primers from a putative transcriptional regulator gene," Res. Microbiol., 156:564-567.
Podbielski et al., Molecular characterization of the cfb gene encoding group B streptococcal CAMP-factor, 1994, Med. Microbiol. Immunol., 183:239-256.
Schoenmakers et al., 1992, Biotechniques, 12:870-874.
Fujishiro et al., 1995, Comput. Biol. Med., 25:61-80.
Bahador et al., 2005, Res. J. Agr. Biol. Sci. 1;142-145.
International Search Report and Written Opinion in corresponding Application No. PCT/US13/44796, dated Nov. 8, 2013, pp. 1-.
El-Harakany AA et al., "Dissociation Constants and Related Thermodynamic Quantities of The Protonated Acid Form of Tris-(Hydroxymethyl)-Aminomethane in Mixtures of 2-Methoxyethanol and Water At Different Temperatures," Journal of Electroanalytical Chemistry:162:285-305 & 296 (1984).

Granholm K. et al., "Desorption of Metal Ions from Kraft Pulps. Part 1. Chelation of Hardwood and Softwood Kraft Pulp With EDTA," Bioresources:5(1)206-226 (2010).
Office Action in corresponding EP Application No. 10180482.1, dated May 30, 2014, pp. 1-5.
Response to the Article 94 in EP Application No. 11184367.8, dated Oct. 23, 2013, pp. 1-12.
Reddy et al., Joints Made by RecA Protein in the Interior of Linear Duplex DNA: Effects of Single-Stranded Ends, Length of Homology, and Dynamic State, *Biochemistry*, 33:11486-11492 (1994).
Toshihiro Horii et al., "Organization of the recA gene of *Escherichia coli*," Proc. Natl. Acad. Sci. USA., 77(1):313-317 (1980).
Examination Report from corresponding European Application No. 11184367.8-1403, dated Aug. 7, 2014, pp. 1-7.
Office Action from corresponding Japanese Application No. 2012-511958, dated Oct. 3, 2014, pp. 1-5.
English translation of Office Action from corresponding Japanese Application No. 2012-511958, dated Oct. 3, 2014, pp. 1-5.
Extended European Search Report in corresponding Application No. 14170595.4, dated Jan. 7, 2015, pp. 1-5.
Notice of Reasons for Rejection in corresponding Application No. JP2012-209422, dated Mar. 3, 2015, pp. 1-15.
Tetart et al., "Phylogeny of the Major Head and Tail Genes of the Wide-Ranging T4-Type Bacteriophages," Journal of Bacteriology, vol. 183(1):358-366 (2001).
Office Action from corresponding Japanese Patent Application No. 2013-029664, dated May 8, 2015, pp. 1-7.
Jill S. Bleuit et al., "Mediator proteins orchestrate enzyme-ssDNA assembly during T4 recombination-dependent DNA replication and repair," PNAS:98(15):8298-8305, Jul. 17, 2001.
Beemink and Morrical, "RMPs: recombination/replication mediator proteins," TIBS Oct. 24, 1999:385-389.
Crannell et al., "Quantification of HIV-1 DNA Using Real-Time Recombinase Polymerase Amplification," American Chemical Society 2014, 86, 5615-5619.
Thomas Kodadek "Functional Interactions Between Phage T4 and *E. coli* DNA-Binding Proteins During the Presynapsis Phase of Homologous Recombination," Biochemical and Biophysical Research Communications, 172(2):804-810 (1990).
Efim I. Golub et al., "Joints formed by RecA protein from oligonucleotides and duplex DNA block initiation and elongation of transcription," Nucleic Acids Research, 20(12):3121-3125 (1992).
Menetski and Kowalczykowski, "Enhancement of *Escherichia coli* RecA Protein Enzymatic Function by dATP," Biochemistry 1989, 28, 5871-5881.
Riddles and Lehman, "The Formation of Paranemic and Plectonemic Joints between DNA Molecules by the recA and Single-stranded DNA-binding Proteins of *Escherichia coli*\*," The Journal of Biological Chemistry, 260(1):165-169 (1985).
Steffen and Bryant, "Reevaluation of the Nucelotide Cofactor Specificity of the RecA Protein from Bacillus subtilis\*," The Journal of Biological Chemistry, 274(37):25990-25994 (1999).
Kozer et al., "Effect of Crowding on Protein-Protein Association Rates: Fundamental Differences between Low and High Mass Crowding Agents," J. Mol. Biol. (2004) 336, 763-774.
Kadyrov et al., "Properties of Bacteriophage T4 Proteins Deficient in Replication Repair," The Journal of Biological Chemistry, 276(27):25247-25255, 2003.
Transmittal of 3$^{rd}$ Party Observations in Application No. 10180482.1, dated Dec. 3, 2015, p. 1.
Third Party Observations under Article 115 EPC in Application No. 10180482, pp. 1-8, dated Nov. 27, 2015.
Third Party Observation for Application No. EP20100180482, pp. 1-2, dated Nov. 27, 2015 16:42.
Third Party Observation for Application No. EP20100180482, pp. 1-2, dated Nov. 27, 2015 16:46.
Third Party Observation for Application No. EP20100180482, pp. 1-2, dated Nov. 27, 2015 16:49.

\* cited by examiner

Figure 1 – Comparison of natural abasic sites, tetrahydrofuran, and dR-O- [C]n structures

Internal dR-Biotin probe is used to test dR cutting by fpg and Nfo enzymes dR biotin probe sequence

5' CAGAAGTATGACCGTGTCTTTGAAATGRTT GAAGAAATGGTT 3' with: 5' = FAM, R = dR-Biotin, 3' = ddC

Internal dR-Biotin can be cut by Nfo and Fpg

SEQUENCE LISTING

<160> NUMBER OF SEQ ID NOS: 16

<210> SEQ ID NO 1
<211> LENGTH: 35
<212> TYPE: DNA
<213> ORGANISM: Artificial Sequence
<220> FEATURE:
<223> OTHER INFORMATION: Synthetic primer

<400> SEQUENCE: 1
acggcattaa caaacgaact gattcatctg cttgg                35

```
<210> SEQ ID NO 2
<211> LENGTH: 35
<212> TYPE: DNA
<213> ORGANISM: Artificial Sequence
<220> FEATURE:
<223> OTHER INFORMATION: Synthetic primer

<400> SEQUENCE: 2
ccttaatttc tccgagaact tcatattcaa gcgtc                              35

<210> SEQ ID NO 3
<211> LENGTH: 43
<212> TYPE: DNA
<213> ORGANISM: Artificial Sequence
<220> FEATURE:
<223> OTHER INFORMATION: Synthetic probe

<400> SEQUENCE: 3
cagaagtatg accgtgtctt tgaaatgrtt gaagaaatgg ttc                     43

<210> SEQ ID NO 4
<211> LENGTH: 33
<212> TYPE: DNA
<213> ORGANISM: Artificial Sequence
<220> FEATURE:
<223> OTHER INFORMATION: Synthetic primer

<400> SEQUENCE: 4
ccatcctcaa tactaagcta agtaaaaaga ttt                                33

<210> SEQ ID NO 5
<211> LENGTH: 33
<212> TYPE: DNA
<213> ORGANISM: Artificial Sequence
<220> FEATURE:
<223> OTHER INFORMATION: Synthetic primer

<400> SEQUENCE: 5
ccctgtggct aagagctctt gatagtcaaa gta                                33

<210> SEQ ID NO 6
<211> LENGTH: 36
<212> TYPE: DNA
<213> ORGANISM: Artificial Sequence
<220> FEATURE:
<223> OTHER INFORMATION: Synthetic probe

<400> SEQUENCE: 6
ccttrtctaa ggaaatggac agaaataggc aagatc                             36

<210> SEQ ID NO 7
<211> LENGTH: 33
<212> TYPE: DNA
<213> ORGANISM: Artificial Sequence
<220> FEATURE:
<223> OTHER INFORMATION: Synthetic primer

<400> SEQUENCE: 7
cccttctgat attctaccaa atgcccccta aat                                33

<210> SEQ ID NO 8
<211> LENGTH: 33
<212> TYPE: DNA
<213> ORGANISM: Artificial Sequence
<220> FEATURE:
<223> OTHER INFORMATION: Synthetic primer
```

<400> SEQUENCE: 8
catgtgtata agaaaactac ccaagcctag gga     33

<210> SEQ ID NO 9
<211> LENGTH: 36
<212> TYPE: DNA
<213> ORGANISM: Artificial Sequence
<220> FEATURE:
<223> OTHER INFORMATION: Synthetic probe

<400> SEQUENCE: 9
cagtgrccaa tacacacaca caagactggg catggc     36

<210> SEQ ID NO 10
<211> LENGTH: 33
<212> TYPE: DNA
<213> ORGANISM: Artificial Sequence
<220> FEATURE:
<223> OTHER INFORMATION: Synthetic primer

<400> SEQUENCE: 10
tatagtggaa aggtgttcat ttgtataaac ccc     33

<210> SEQ ID NO 11
<211> LENGTH: 33
<212> TYPE: DNA
<213> ORGANISM: Artificial Sequence
<220> FEATURE:
<223> OTHER INFORMATION: Synthetic primer

<400> SEQUENCE: 11
cacataaatc agagaatgtg tggggtcatg tat     33

<210> SEQ ID NO 12
<211> LENGTH: 36
<212> TYPE: DNA
<213> ORGANISM: Artificial Sequence
<220> FEATURE:
<223> OTHER INFORMATION: Synthetic probe

<400> SEQUENCE: 12
aacttrgcaa ctaacgctaa attataatca cttctc     36

<210> SEQ ID NO 13
<211> LENGTH: 33
<212> TYPE: DNA
<213> ORGANISM: Artificial Sequence
<220> FEATURE:
<223> OTHER INFORMATION: Synthetic primer

<400> SEQUENCE: 13
catttctcaa aagaagatat gcaaataaaa aca     33

<210> SEQ ID NO 14
<211> LENGTH: 33
<212> TYPE: DNA
<213> ORGANISM: Artificial Sequence
<220> FEATURE:
<223> OTHER INFORMATION: Synthetic primer

<400> SEQUENCE: 14
ccattataac tggggtgaga tgatatctca ttg     33

<210> SEQ ID NO 15
<211> LENGTH: 36

```
<212> TYPE: DNA
<213> ORGANISM: Artificial Sequence
<220> FEATURE:
<223> OTHER INFORMATION: Synthetic probe

<400> SEQUENCE: 15
tctcarcata actgatcatc agagaaatgt aaatcc                          36

<210> SEQ ID NO 16
<211> LENGTH: 8
<212> TYPE: PRT
<213> ORGANISM: Artificial Sequence
<220> FEATURE:
<223> OTHER INFORMATION: FLAG-peptide

<400> SEQUENCE: 16

Asp Tyr Lys Asp Asp Asp Asp Lys
1               5
```

US 9,896,719 B2

DNA GLYCOSYLASE/LYASE AND AP ENDONUCLEASE SUBSTRATES

RELATED APPLICATIONS

This application is a continuation and claims the benefit of priority to U.S. patent application Ser. No. 12/800,633, filed May 18, 2010, which claims the benefit of priority to U.S. Provisional Patent Application No. 61/179,793 filed May 20, 2009, which is hereby incorporated by reference in its entirety.

FIELD OF THE INVENTION

This invention relates to oligonucleotide substrates, as well as for their uses, for example, as probes for nucleic acid amplification reactions.

BACKGROUND OF THE INVENTION

Enzymes which metabolize nucleic acids in a manner specified by primary sequence, backbone structure, or a base character (often damaged or modified base) are of utility in biotechnology applications. Several families of such enzymes are used routinely in nucleic acid-based techniques and include restriction endonucleases, polymerases, ligases and exonucleases. Additionally, a variety of single-subunit (non-restriction) endonucleases which rely not on specific sequence strings but on recognising unusual, damaged or missing bases have been described over the years. These enzymes can be loosely divided into 2 groups—the AP endonucleases, of which E. coli endonuclease IV (Nfo) and E. coli exonuclease III are examples, and the DNA glycosylase/lyase family of which E. coli fpg, MUG and Nth are examples.

The AP endonucleases are characterised by the ability to recognise and cleave the sugar-phosphate backbone at abasic sites (other enzymatic activities may also be present) when found in the context of duplex DNA. Recognition and incision at abasic sites occurs in a biochemical manner that is distinct to the glycosylase/lyase family and not by beta-elimination or beta/delta-elimination. Consequently they attack not only true abasic sites but other substrates including tetrahydrofuran moieties which lack an oxygen atom on the 1' carbon of the sugar ring (Takeshita et al., 1987, J Biol Chem. 262(21):10171)(see FIG. 1 for chemical structures).

In contrast, glycosylase/lyase enzymes including the fpg protein (8-oxoguanine DNA glycosylase, fpg in E. coli and OGG1 in mammals) or Nth proteins (endonuclease III in E. coli, Nth1 in humans, etc.) function in a 2-stage catalytic manner in which damaged bases are first recognized and excised via formation of a Schiff base between the protein and the DNA, and secondly the abasic site thus generated is processed by beta-elimination or beta-delta elimination in a manner distinct to the AP endonucleases. In this case tetrahydrofuran (THF) residues are not a substrate for lyase activity as no C1' oxygen atom is present in this abasic mimic and such sugars lacking oxygen at the 1' position are resistant to attack (Takeshita et al., 1987)(FIG. 1).

The use of AP endonucleases and glycosylase/lyases in molecular biology techniques has been described. One application is the use of these enzymes to process substrates generated during in vitro DNA amplification reactions, or similar kinds of applications, and in particular when a synthetic 'probe' oligonucleotide has been provided containing modified sugars or bases which can become a substrate for the enzymes if the synthetic oligonucleotide hybridizes specifically to molecules in the sample. An example of such an application is given in U.S. Pat. No. 7,435,561 B2 and Piepenburg et al., Plos Biology, 2006 4(7):e204 in which tetrahydrofuran-modified oligonucleotides are used as substrates for the E. coli Nfo (endonuclease IV) protein as a method to measure DNA amplification (Nfo is one of the two AP endonucleases of E. coli).

Application of glycosylase/lyases to similar strategies can also be envisioned. The ability of fpg protein to similarly process modified bases such as 8-oxoguanine within a DNA amplification reaction for the purposes of reaction-monitoring has been described (U.S. Pat. No. 7,435,561 B2). Furthermore the fact that glycosylase/lyase enzymes such as fpg and Nth do not leave 3' extendable ends but rather blocked 3' ends (due to the differences in catalytic mode) may have particular utility in circumstances in which one wishes to ensure that the processed probe cannot be a ready substrate for polymerases or other activities dependent on a 3' hydroxyl moiety.

Despite the potential of these enzymes, they possess certain features that make them unattractive for use in some applications. Notably, unlike the THF residue, true abasic sites required for the backbone-incising activity of DNA lyases are not stable under physiological conditions and are quickly hydrolyzed in aqueous solutions making them impractical for use in most molecular procedures. Instead specific damaged bases can be incorporated and used as the primary substrates for the glycosylase activity to generate the abasic site transiently before backbone hydrolysis by the lyase activity. Unfortunately however, typical damaged base analogs such as 8-oxoguanine (fpg) or thymidine glycol (Nth) tend to be rather expensive to synthesize and also impart sequence requirements on the probe as ideally they must be paired opposite specific bases on the opposing strand. In principle it would be far more convenient to have a stable substrate analogous to the generic THF residue that can be employed for AP endonucleases but retaining reactivity with the lyase activity of glycosylase/lyase enzymes.

Here we show that the fpg protein, as well as the AP endonuclease IV of E. coli (Nfo), efficiently cleaves DNA backbones containing a variety of substrates that lack a base but contain a 1'-oxygen atom covalently attached to a carbon-based linker [C]n. The linker can itself be used to attach other moieties such as biotin, fluorophores and other coupled groups, particularly useful if an amine-ended linker can be used to couple a variety of agents. Surprisingly, nucleotides having this arrangement and referred to generally as dR-O—[C]n appear to be good substrates of the fpg protein in a number of contexts, and are also substrates for the endonuclease IV protein, but appear relatively poor substrates for E. coli exonuclease III. We anticipate the use of oligonucleotides containing such dR-O—[C]n groups as substrates in a number of circumstances, in particular within in vitro reactions such as part of detection strategies for nucleic acid detection methods. The length of the linker used in this study is 6 carbon atoms, as available on certain commercially available nucleotides, however it is anticipated that a variety of carbon chain lengths might be employed and that it is the carbon-oxygen-carbon structure with little subsequent steric bulking that affords these structures sufficient plasticity to the enzymes.

SUMMARY OF THE INVENTION

The present invention relates in part to the discovery that AP endonucleases, DNA glycosylases, an DNA glycosylase/lyases, such as fpg and Nfo proteins, can catalyze the breaking of the DNA backbone at sites containing dR-O—[C]n residues in which no base is present at the C1' position of the sugar, but that retains an oxygen atom at that position. The oxygen atom bridges the sugar to a carbon atom of a carbon linker with n (e.g., 1-8) carbon atoms (i.e., [C]n). Consequently nucleic acid probes can be constructed containing dR-O—[C]n residues by the use of commercially available phosphoramidites and can be substrates for AP endonucleases and DNA glycosylase/lyase enzymes if they form duplexes with complementary nucleic acids. A variety of moieties may be coupled to the linker portion of the dR-O—[C]n including fluorophores and other labels suggesting a number of strategies to detect successful processing of the probe as evidence of presence of a specific target nucleic acid. Applicants show how probes may be constructed using fluorescent molecules and quenchers using dR-O—[C]n as targeting sites for fpg, Nfo or other potential AP endonucleases or lyases. Applicants contemplate other uses of the dR-O—[C]n substrates in other detection schemes. For example, the dR-O—[C]n residue may be conjugated to a detactable label, where the activity of the nuclease frees the label, which can then be detected either immediately or via a subsequent process, via a measurable difference between the conjugated and free state.

In one aspect, processes are provided herein for cleaving an oligonucleotide containing a dR-O—[C]n residue that forms a duplex with a nucleic acid, by contacting the duplex with a nuclease selected from an AP endonucleases, or DNA glycosylases, or an DNA glycosylase/lyases. In some embodiments, the nuclease is endonuclease IV (Nfo) or 8-oxoguanine DNA glycosylase (fpg). In some embodiments, the linker is a 3-6 carbon atom linker (e.g., a 6 carbon atom linker). In some embodiments, the oligonucleotide is blocked at its 3'-end to prevent polymerase extension. In some embodiments, the linker is conjugated to a detectable label (e.g., biotin, digoxygenin, peptide, fluorophore, quencher, antibody or a quantum dot).

In some embodiments, the process further comprises the step of contacting the oligonucleotide with the nucleic acid to form the oligonucleotide/nucleic acid duplex. In some embodiments, this comprises hybridizing the oligonucleotide to the nucleic acid. In some embodiments, this comprises (i) contacting the oligonucleotide with a recombinase to form a recombinase/oligonucleotide complex; and (ii) contacting the recombinase/oligonucleotide complex to the nucleic acid to form the oligonucleotide/nucleic acid duplex. In some embodiments, the nucleic acid is the product of a nucleic acid amplification reaction (e.g., a recombinase polymerase amplification (RPA) process or a polymerase chain reaction (PCR)).

In some embodiments, the process further comprises the step of detecting cleavage of the oligonucleotide. In some embodiments, the detection is monitored in real time. In some embodiments, the detection is monitored at an endpoint for the reaction.

In some embodiments, the oligonucleotide contains a fluorophore and a quencher, where one of the fluorophore or the quencher is conjugated to the carbon linker. The nuclease activity excises the conjugated fluorophore or quencher from the oligonucleotide and the detection step comprises measuring a difference, if any, in fluorescence between the conjugated and free state.

In another aspect, processes are provided herein for detecting the presence or absence of a target nucleic acid. The processes comprise the following steps: (a) contacting an oligonucleotide probe containing a dR-O—[C]n residue or nucleotide with the target nucleic acid to form a probe/nucleic acid duplex; (b) contacting the duplex with a nuclease selected from an AP endonucleases, or DNA glycosylases, or an DNA glycosylase/lyases to excise the linker from the complex and/or specifically cleave the probe at the dR-O—[C]n nucleotide; and (c) detecting whether such excision or cleavage has occurred. In some embodiments, the nucleic acid is the product of a nucleic acid amplification reaction (e.g., a recombinase polymerase amplification (RPA) process or a polymerase chain reaction (PCR)). In some embodiments, the amplification reaction is monitored in real time. In some embodiments, the amplification reaction is monitored at an endpoint for the reaction.

In some embodiments, the duplex is formed by hybridizing the probe to the nucleic acid. In some embodiments, the duplex is formed by (i) contacting the probe with a recombinase to form a recombinase/probe complex; and (ii) contacting the recombinase/probe complex to the nucleic acid to form the probe/nucleic acid duplex.

In some embodiments, the nuclease is endonuclease IV (Nfo) or 8-oxoguanine DNA glycosylase (fpg). In some embodiments, the linker is a 3-6 carbon atom linker (e.g., a 6 carbon atom linker). In some embodiments, the oligonucleotide is blocked at its 3'-end to prevent polymerase extension. In some embodiments, the linker is conjugated to a detectable label (e.g., biotin, digoxygenin, peptide, fluorophore, quencher, antibody or a quantum dot).

In some embodiments, the probe contains a fluorophore and a quencher, where one of the fluorophore or the quencher is conjugated to the carbon linker. For example, the fluorophore and the quencher are separated by 4-6 bases in the probe. In some embodiments, the fluorophore or the quencher that is not conjugated to the carbon linker is conjugated to the end (e.g., the 5'-end) of the probe. The nuclease activity excises and frees the conjugated fluorophore or quencher associated with the dR-O—[C]n residue from the probe and the detection step comprises measuring a difference, if any, in fluorescence between the conjugated and free state.

In another aspect, provided herein are oligonucleotide probes containing a dR-O—[C]n residue. In some embodiments, the probes are 30 to 60 nucleotides in length and contain a fluorophore quencher pair separated by 10 nucleotides or less (e.g., 4-6 nucleotides), where either the fluorophore or the quencher is conjugated to the dR-O—[C]n residue. In some embodiments, the linker is a 3-6 carbon atom linker (e.g., a 6 carbon atom linker). In some embodiments, the oligonucleotide is blocked at its 3'-end to prevent polymerase extension. In some embodiments, the fluorophore or the quencher that is not conjugated to the dR-O—[C]n residue is conjugated to the end (e.g., the 5'-end) of the probe. In some embodiments, the probes are 30 to 40 nucleotides (e.g., 35 nucleotides) in length.

In yet another aspect, provided herein are kits comprising (i) an oligonucleotide containing a dR-O—[C]n residue, and (ii) a nuclease selected from an AP endonucleases, or DNA glycosylases, or an DNA glycosylase/lyases. In some embodiments, the nuclease is endonuclease IV (Nfo) or 8-oxoguanine DNA glycosylase (fpg).

In yet a further aspect, provided herein are reaction mixtures comprising an oligonucleotide containing a dR-O—[C]n residue and a nuclease selected from an AP endonucleases, or DNA glycosylases, or an DNA glycosylase/lyases (e.g., endonuclease IV (Nfo) or 8-oxoguanine DNA glycosylase (fpg)). In some embodiments, the linker is a 3-6 carbon atom linker (e.g., a 6 carbon atom linker). In some embodiments, the oligonucleotide is blocked at its 3'-end to prevent polymerase extension. In some embodiments, the linker is conjugated to a detectable label (e.g., biotin, digoxygenin, peptide, fluorophore, quencher, antibody or a quantum dot). In some embodiments, the reaction mixture is freeze dried or lyophilized.

In some embodiments, the reaction mixture further comprises a container. For example, the reaction mixture can be contained in a tube or in a well of a multi-well container. The reaction mixtures may be dried or attached onto a mobile solid support such as a bead or a strip, or a well.

In some embodiments, the reaction mixture further comprises a target or template nucleic acid that contains a sequence that is complementary to the oligonucleotide.

Other embodiments, objects, aspects, features, and advantages of the invention will be apparent from the accompanying description and claims. It is contemplated that whenever appropriate, any embodiment of the present invention can be combined with one or more other embodiments of the present invention, even though the embodiments are described under different aspects of the present invention.

DETAILED DESCRIPTION OF THE INVENTION

Figure 1:
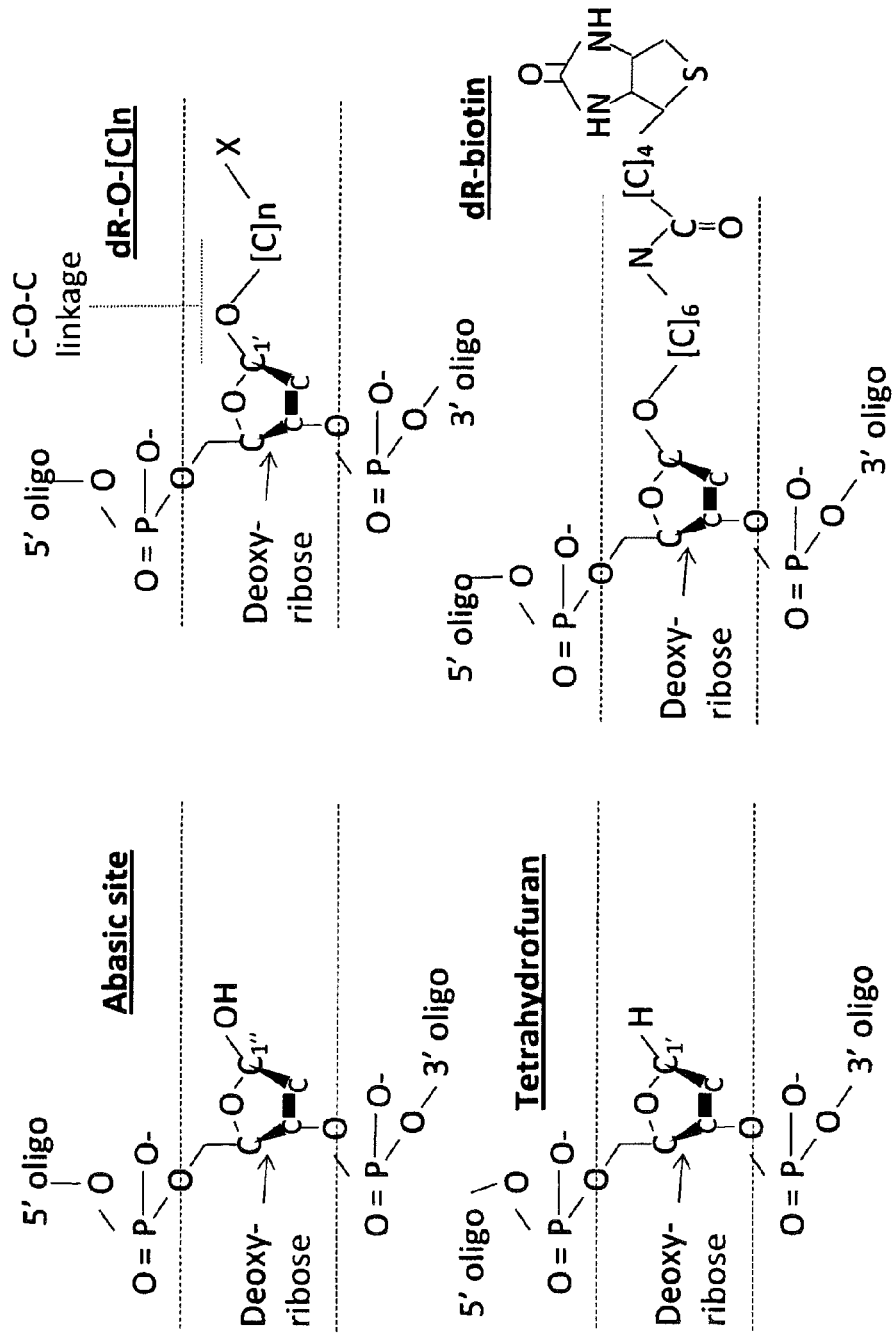
FIG. 1 Chemical structures: general structure of a normal abasic site containing a hydroxyl at the 1' carbon position, of a tetrahydrofuran (THF) residue containing a hydrogen at the 1' position, of the general dR-O—[C]n group indicating the position of the carbon-oxygen-carbon bridge between the C1' of the DNA ribose group and the linker to the attached marker moiety, and finally of the dR-biotin nucleotide used in Example 1 and conforming to the dR-O—[C]n structure described.

The details of one or more embodiments of the invention are set forth in the accompanying description below. Although any methods and materials similar or equivalent to those described herein can be used in the practice or testing of the present invention, the methods and materials are now described. Other features, objects, and advantages of the invention will be apparent from the description. In the specification, the singular forms also include the plural unless the context clearly dictates otherwise. Unless defined otherwise, all technical and scientific terms used herein have the same meaning as commonly understood by one of ordinary skill in the art to which this invention belongs. In the case of conflict, the present Specification will control.

The combination of enzymes with synthetic substrates for use in laboratory assays and manipulations is well known in the art. DNA repair endonucleases such as the glycosylases fpg and Nth, as well as AP endonucleases such as E. coli exonuclease III and endonuclease IV, are good examples of this combination—it is easy to generate synthetic substrates for these DNA repair enzymes by the use of modern oligonucleotide synthesis regimes and the wide existing variety of synthetic nucleotides that may be incorporated into DNA primers. These DNA repair enzymes can be readily employed for a variety of purposes, and one which has been recently exploited is their use as agents to assist the monitoring of isothermal Recombinase Polymerase Amplification (RPA) reactions.

RPA is a process in which recombinase-mediated targeting of oligonucleotides to DNA is coupled to DNA synthesis by a polymerase (U.S. Pat. No. 7,270,981 B2; U.S. Pat. No. 7,399,590; U.S. Pat. No. 7,435,561 B2; U.S. Pat. No. 7,485,428 B2; U.S. Pat. No. 7,666,598 B2 and foreign equivalents). RPA depends upon components of the cellular DNA replication and repair machinery, and relies upon establishment of a 'dynamic' recombination environment having adequate rates of both recombinase loading and unloading that maintains high levels of recombination activity achieved in the presence of specific crowding agents. RPA has the advantage that it combines the sensitivity, specificity and most other features of PCR but without the need for thermocycling and with extraordinary speed and robustness to off-temperature set-up. RPA has already benefited from the potential employment of a wide variety of nucleic acid processing enzymes such as known repair endonucleases which have been untapped by other processes because of either the need for thermostable equivalents or because they demonstrate poor regulation without accessory proteins such as single-stranded DNA binding proteins, a natural component of RPA reactions.

Briefly, RPA comprises the following steps: First, a recombinase agent is contacted with a first and a second nucleic acid primer to form a first and a second nucleoprotein primer. Second, the first and second nucleoprotein primers are contacted to a double stranded target sequence to form a first double stranded structure at a first portion of said first strand and form a double stranded structure at a second portion of said second strand so the 3' ends of said first nucleic acid primer and said second nucleic acid primer are oriented towards each other on a given template DNA molecule. Third, the 3' end of said first and second nucleoprotein primers are extended by DNA polymerases to generate first and second double stranded nucleic acids, and first and second displaced strands of nucleic acid. Finally, the second and third steps are repeated until a desired degree of amplification is reached.

Earlier work has demonstrated the extreme utility of the synthetic nucleotide tetrahydrofuran (THF) in the development of probe systems for the RPA method (Piepenburg et al., 2006; U.S. Pat. No. 7,435,561 B2). This base analog is oftentimes used to mimic abasic sites and has the natural advantage that it is stable—replacement of the 1'-hydroxyl of a natural abasic site with a hydrogen atom renders the nucleotides stable and unable to undergo spontaneous ring-opening and oligonucleotide fragmentation. This analog is readily available and cheap to incorporate into oligonucleotides. Due to differences in biochemical mechanism, however, while the E. coli AP endonucleases Nfo and ExoIII can cleave at such THF residues in synthetic primers, other DNA glycoslyase/lyases cannot. These latter enzymes normally require a damaged base (glycosylase activity) and/or the presence of a hydroxyl group at the 1'-position of the sugar (lyase activity) and THF is completely inert to their enzymatic activities. This presents something of a nuisance as these glycosylase/lyase enzymes could be useful tools also for in vitro reactions such as those in which a probe is processed in response to target DNA accumulation in RPA, or in other contexts and methods. More natural substrates, for example 8-oxoguanine for fpg, can be inserted into oligonucleotides to generate cleavage sites for these glycosylase/lyases, however these modifications are usually expensive, and furthermore often restrict the base which can be opposed to the modified nucleotide. Cheaper and more general nucleotide modifications which are substrates for these enzymes would be of great utility.

In an effort to explore the effects of a number of unusual base analogs as substrates for DNA repair enzymes we synthesised oligonucleotides containing nucleotides completely lacking a base, but retaining a carbon-oxygen-carbon linkage at the 1' position of the sugar. Such nucleotide reagents are readily available and inexpensive, and are commonly used to incorporate labelling groups such as fluorophores or biotin into oligonucleotides within the body of the oligonucleotide. Commonly the carbon atom linked through oxygen to the 1' carbon of the sugar is the first carbon atom of a linker which often ultimately ends with the labelling group, or alternatively an amine or other chemical moiety (e.g., a thiol) to which reagents may be readily coupled. Such reagents are often described in the literature as dR-X in which the dR refers to deoxyribose, and the X will often be linker-amine, or linker-fluorophore, or linker-biotin, or some other group or label. No-one has previously explored whether or not repair endonucleases would recognise such structures which lack a base but retain a carbon-oxygen-carbon covalent linkage at the 1' sugar position. The absence of a hydroxyl means that the ring-opening processes of lyases should not operate without prior processing of the linker group and its associated excision. As known glycosylases normally operate on damaged bases rather than unusual carbon linkers there was no precedent to suggest that these dR-O—[C]n groups would be substrates for DNA glycosylase/lyases such as fpg.

FIG. 1 shows the general structure of a dR-O—[C]n group, as well as specifically the structure of the dR-biotin reagents as incorporated into oligonucleotides used herein and purchased from Eurogentec, Belgium. Such reagents used herein have a common 6 carbon atom linker between the 1'-sugar and a nitrogen atom which is often used to couple other reagents before or after oligonucleotide synthesis. In this study the biotin moiety of the dR-biotin oligonucleotide is linked via this nitrogen atom as an amide bond and then through a further 4 carbon atom linker. Other label reagents used in this study—dR-FAM and dR-Texas Red—are similarly arranged in which a fluorophore is coupled through an amide bond at the end of the 6 carbon atom linker.

A detectable label is defined as any moiety that may be detected using current methods. These labels include, at least, a fluorophore (also called a fluorescent molecule, fluorochrome), an enzyme, a quencher, an enzyme inhibitor, a radioactive label, a member of a binding pair, a digoxygenin residue, a peptide, and a combination thereof.

"A member of a binding pair" is meant to be one of a first and a second moiety, wherein said first and said second moiety have a specific binding affinity for each other. Suitable binding pairs for use in the invention include, but are not limited to, antigens/antibodies (for example, digoxigenin/anti-digoxigenin, dinitrophenyl (DNP)/anti-DNP, dansyl-X-anti-dansyl, Fluorescein/anti-fluorescein, lucifer yellow/anti-lucifer yellow, peptide/anti-peptide, ligand/receptor and rhodamine/anti-rhodamine), biotin/avidin (or biotin/streptavidin) and calmodulin binding protein (CBP)/calmodulin. Other suitable binding pairs include polypeptides such as the FLAG-peptide (DYKDDDDK; SEQ ID NO: 16) [Hopp et al., BioTechnology, 6:1204 1210 (1988)]; the KT3 epitope peptide (Martin et al., Science 255:192 194 (1992)); tubulin epitope peptide (Skinner et al., J. Biol. Chem 266:15163 15166 (1991)); and the T7 gene 10 protein peptide tag (Lutz-Freyermuth et al., Proc. Natl. Acad. Sci. USA, 87:6393 6397 (1990)) and the antibodies each thereto. Generally, in a preferred embodiment, the smaller of the binding pair partners serves as the detectable label, as steric considerations may be important.

In one aspect, processes are provided herein for cleaving an oligonucleotide containing a dR-O—[C]n residue that forms a duplex with a nucleic acid, by contacting the duplex with a nuclease selected from an AP endonucleases, or DNA glycosylases, or an DNA glycosylase/lyases. In some embodiments, the nuclease is endonuclease IV (Nfo) or 8-oxoguanine DNA glycosylase (fpg). In some embodiments, the linker is a 3-6 carbon atom linker (e.g., a 6 carbon atom linker). In some embodiments, the oligonucleotide is blocked at its 3'-end to prevent polymerase extension. In some embodiments, the linker is conjugated to a detectable label (e.g., biotin, digoxygenin, peptide, fluorophore, quencher, antibody or a quantum dot).

In some embodiments, the process further comprises the step of contacting the oligonucleotide with the nucleic acid to form the oligonucleotide/nucleic acid duplex. In some embodiments, this comprises hybridizing the oligonucleotide to the nucleic acid. In some embodiments, this comprises (i) contacting the oligonucleotide with a recombinase to form a recombinase/oligonucleotide complex; and (ii) contacting the recombinase/oligonucleotide complex to the nucleic acid to form the oligonucleotide/nucleic acid duplex. In some embodiments, the nucleic acid is the product of a nucleic acid amplification reaction (e.g., a recombinase polymerase amplification (RPA) process or a polymerase chain reaction (PCR)).

In some embodiments, the process further comprises the step of detecting cleavage of the oligonucleotide. In some embodiments, the detection is monitored in real time. In some embodiments, the detection is monitored at an endpoint for the reaction.

In some embodiments, the oligonucleotide contains a fluorophore and a quencher, where one of the fluorophore or the quencher is conjugated to the carbon linker. The nuclease activity excises the conjugated fluorophore or quencher from the oligonucleotide and the detection step comprises measuring a difference, if any, in fluorescence between the conjugated and free state.

In another aspect, processes are provided herein for detecting the presence or absence of a target nucleic acid. The processes comprise the following steps: (a) contacting an oligonucleotide probe containing a dR-O—[C]n residue or nucleotide with the target nucleic acid to form a probe/nucleic acid duplex; (b) contacting the duplex with a nuclease selected from an AP endonucleases, or DNA glycosylases, or an DNA glycosylase/lyases to excise the linker from the complex and/or specifically cleave the probe at the dR-O—[C]n nucleotide; and (c) detecting whether such excision or cleavage has occurred. In some embodiments, the nucleic acid is the product of a nucleic acid amplification reaction (e.g., a recombinase polymerase amplification (RPA) process or a polymerase chain reaction (PCR)). In some embodiments, the amplification reaction is monitored in real time. In some embodiments, the amplification reaction is monitored at an endpoint for the reaction.

In some embodiments, the duplex is formed by hybridizing the probe to the nucleic acid. In some embodiments, the duplex is formed by (i) contacting the probe with a recombinase to form a recombinase/probe complex; and (ii) contacting the recombinase/probe complex to the nucleic acid to form the probe/nucleic acid duplex.

In some embodiments, the nuclease is endonuclease IV (Nfo) or 8-oxoguanine DNA glycosylase (fpg). In some embodiments, the linker is a 3-6 carbon atom linker (e.g., a 6 carbon atom linker). In some embodiments, the oligonucleotide is blocked at its 3'-end to prevent polymerase extension. In some embodiments, the linker is conjugated to a detectable label (e.g., biotin, digoxygenin, peptide, fluorophore, quencher, antibody or a quantum dot).

In some embodiments, the probe contains a fluorophore and a quencher, where one of the fluorophore or the quencher is conjugated to the carbon linker. For example, the fluorophore and the quencher are separated by 4-6 bases in the probe. In some embodiments, the fluorophore or the quencher that is not conjugated to the carbon linker is conjugated to the end (e.g., the 5'-end) of the probe. The nuclease activity excises and frees the conjugated fluorophore or quencher associated with the dR-O—[C]n residue from the probe and the detection step comprises measuring a difference, if any, in fluorescence between the conjugated and free state.

In another aspect, provided herein are oligonucleotide probes containing a dR-O—[C]n residue. In some embodiments, the probes are 30 to 60 nucleotides in length and contain a fluorophore quencher pair separated by 10 nucleotides or less (e.g., 4-6 nucleotides), where either the fluorophore or the quencher is conjugated to the dR-O—[C]n residue. In some embodiments, the linker is a 3-6 carbon atom linker (e.g., a 6 carbon atom linker). In some embodiments, the oligonucleotide is blocked at its 3'-end to prevent polymerase extension. In some embodiments, the fluorophore or the quencher that is not conjugated to the dR-O—[C]n residue is conjugated to the end (e.g., the 5'-end) of the probe. In some embodiments, the probes are 30 to 40 nucleotides (e.g., 35 nucleotides) in length.

In yet another aspect, provided herein are kits comprising (i) an oligonucleotide containing a dR-O—[C]n residue, and (ii) a nuclease selected from an AP endonucleases, or DNA glycosylases, or an DNA glycosylase/lyases. In some embodiments, the nuclease is endonuclease IV (Nfo) or 8-oxoguanine DNA glycosylase (fpg).

In yet a further aspect, provided herein are reaction mixtures comprising an oligonucleotide containing a dR-O—[C]n residue and a nuclease selected from an AP endonucleases, or DNA glycosylases, or an DNA glycosylase/lyases (e.g., endonuclease IV (Nfo) or 8-oxoguanine DNA glycosylase (fpg)). In some embodiments, the linker is a 3-6 carbon atom linker (e.g., a 6 carbon atom linker). In some embodiments, the oligonucleotide is blocked at its 3'-end to prevent polymerase extension. In some embodiments, the linker is conjugated to a detectable label (e.g., biotin, digoxygenin, peptide, fluorophore, quencher, antibody or a quantum dot). In some embodiments, the reaction mixture is freeze dried or lyophilized.

In some embodiments, the reaction mixture further comprises a container. For example, the reaction mixture can be contained in a tube or in a well of a multi-well container. The reaction mixtures may be dried or attached onto a mobile solid support such as a bead or a strip, or a well.

In some embodiments, the reaction mixture further comprises a target or template nucleic acid that contains a sequence that is complementary to the oligonucleotide.

Figure 2:
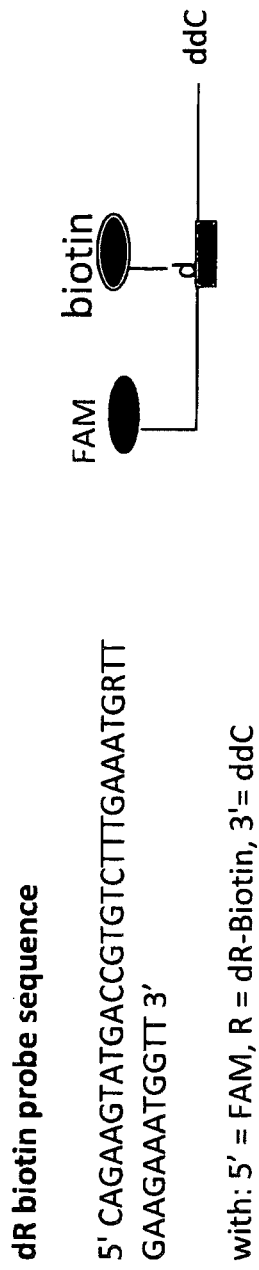
FIG. 2 dR-biotin probe design: sequence (SEQ ID NO:3) and schematic representation of the oligonucleotide probe used to assess cleavage activity of Nfo and fpg proteins during RPA reactions in which a target sequence matching the probe sequence is amplified. The sequence of the oligonucleotide is indicated. The primer is labelled at the 5' end with the FAM fluorophore, contains a dR-biotin within the body of the sequence, and is blocked by virtue of a 2',3'-dideoxycytidine residue.
Figure 3:
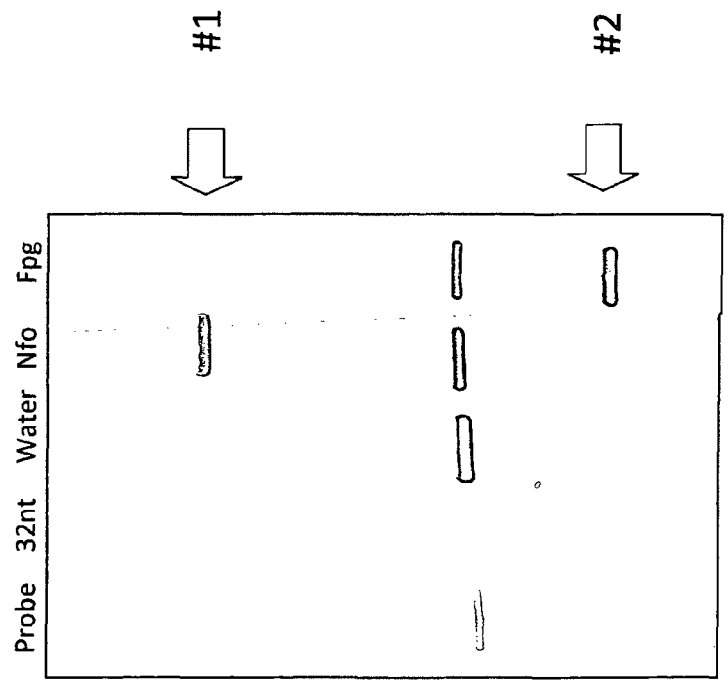
FIG. 3 Comparison of amplification reactions lacking nuclease or containing Nfo or fpg enzyme: reveals that both enzymes can process the dR-biotin moiety giving rise to a faster migrating cleavage product and in the case of Nfo a product produced by extension of the cleavage product.

FIG. 2 indicates both primary sequence and schematically the nature of a dR-biotin probe generated for use in an RPA DNA amplification reaction using as a target a DNA molecule containing the sequence specified in the probe. The probe is blocked (to prevent polymerase extension during the amplification phase) and contains an internal dR-biotin as the test substrate for the enzymes. The probe also contains a 5'-FAM. Thus, in principle, if DNA is amplified in a reaction containing this probe there is the possibility that the probe will bind to and interact specifically with the amplified DNA either by 'classical' hybridization to complementary single strands formed during amplification, or by recombinase-mediated processes. The outcome of such an experiment is shown in FIG. 3 and described in Example 1 below.

Figure 4:
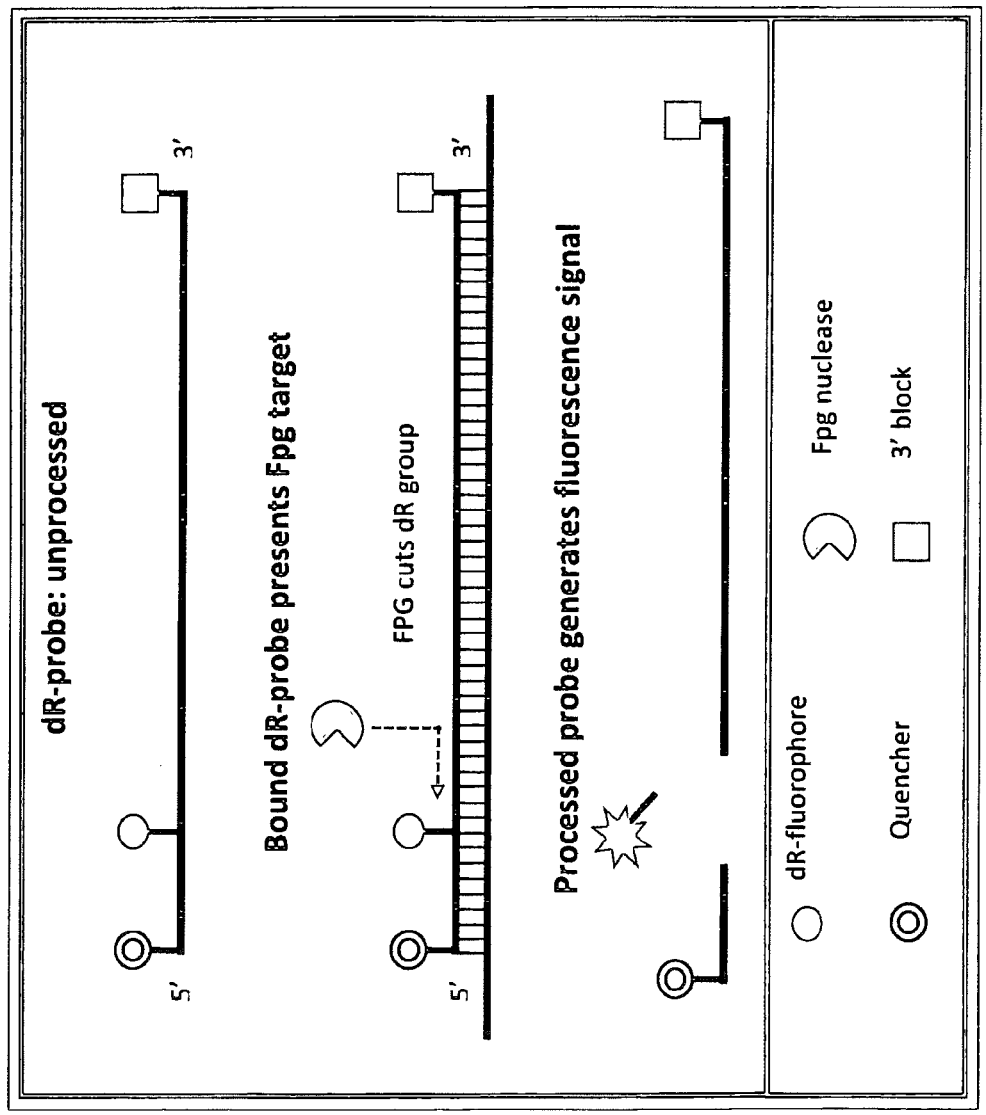
FIG. 4 Oligonucleotide probe design: example of a probe design, including an oligonucleotide body (here 35 nucleotides in length), a 5'-quencher modification (here a 5'-BHQ1), an internal dR-fluorophore nucleotide analogue in proximity to the quencher (here a dR-FAM at oligonucleotide position 6) and a 3' polymerase extension block.
Figure 5:
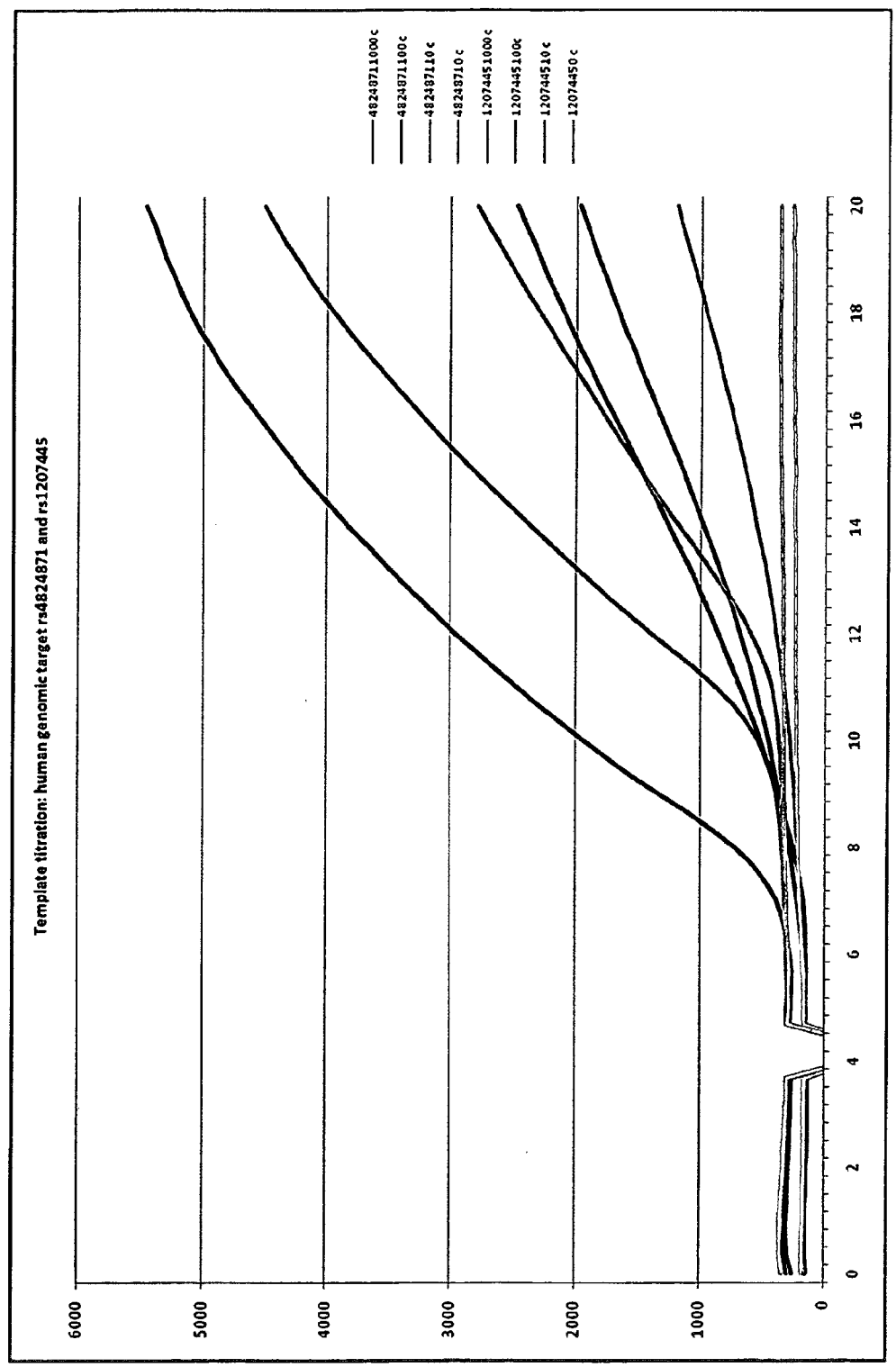
FIG. 5 Sensitivity and specificity: results of real-time fluorescence monitoring of two template titration experiments for the indicated human genomic targets using DNA dR-probes. In both cases the increase of fluorescence signal (relative to the baseline at 0 to 3 minutes) is only observed in reactions containing template and not in the no-template control. The onset time of the signal increase correlates with the amount of starting template (1000, 100 or 10 copies). Reaction time is in minutes (X-axis), fluorescence in arbitrary fluorescence units (Y-axis).
Figure 6:
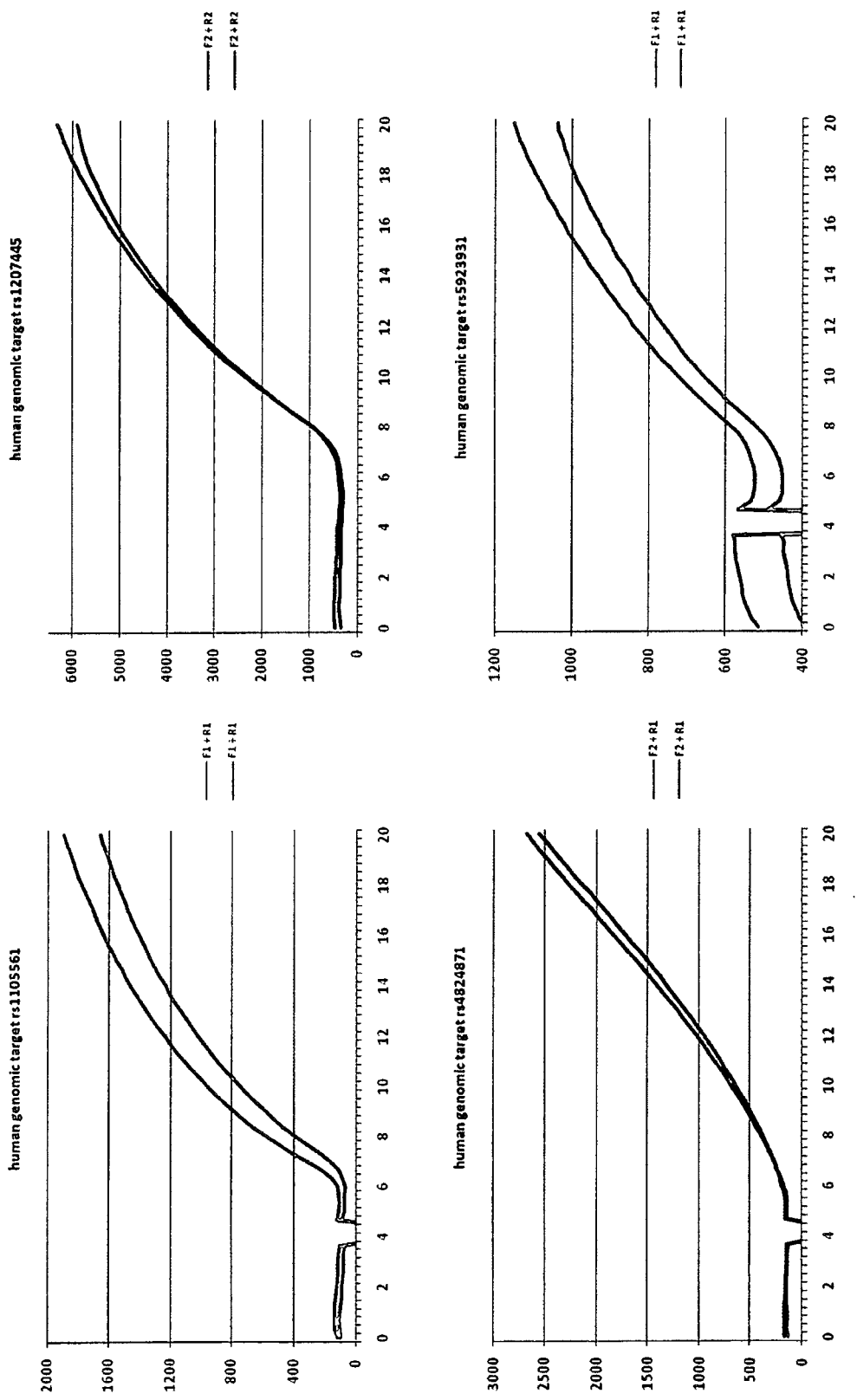
FIG. 6 Performance of different probes: results of real-time fluorescence monitoring of four sets of RPA reactions (in duplicates) for the indicated human genomic targets using DNA oligonucleotide probes of the design outlined in FIG. 2. The increase in fluorescence between 6 and 8 minutes results from the fpg-dependent processing of the dR-groups of the probes (here dR-FAM) and indicates ongoing DNA amplification and thus the presence of the target DNA template. Reaction time is in minutes (X-axis), fluorescence in arbitrary fluorescence units (Y-axis).

A second set of experiments was performed to investigate the generality of this cleavage activity, and in this case using fluorescent reagents in which the dR-O—[C]n nucleotide is coupled to a fluorophore as depicted in FIG. 4. In this case the dR-fluorophore is positioned close to the 5' end of the oligonucleotide probe and in close proximity to a quencher which is attached to the very 5' end. As before the 3' end of the probe is suitably blocked to prevent aberrant elongation or primer artefacts. As indicated in FIG. 4, should the probe form hybrids with complementary amplifying material then it might become a substrate for fpg (or Nfo) and if so could cleave the backbone at this position (and potentially release the fluorophore directly into the aqueous medium detached from either oliogonucleotide fragment if the glycosylase activity is present in fpg or other non-AP endonuclease enzymes). If cleavage occurs there will be physical separation of the fluorophore and quencher and hence an increase in detectable fluorescence in a manner akin to that described earlier for THF-based fluorescent probes utilising E. coli Nfo or exoIII proteins. FIGS. 5 and 6 show the outcome of such experiments and describe in Example 2 in which RPA reactions were performed on human genomic targets utilizing primers and probes specifically directed toward known single nucleotide polymorphism (SNP) regions.

These experiments collectively clearly demonstrate that dR-O—[C]n groups are substrates for the Nfo and the fpg nucleases. Furthermore, it is possible to construct probes containing such groups in a way that the activity of the nucleases on the probe occurs only in the circumstance that complementary nucleic acid strands accumulate permitting duplex formation, thereby allowing determination of whether the amplification has occurred by fluorescence or other mechanisms. Therefore, these dR-O—[C]n nucleotide reagents could be broadly applied in combination with fpg, Nfo or glycosylase/lyase and equivalent enzymes for a variety of uses.

All sequence citations, references, patents, patent applications or other documents cited are hereby incorporated by reference.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

Example 1

Oligonucleotides Probes Containing an Internal dR-Biotin are Cut by Nfo and Fpg

In this example it is shown that oligonucleotides probes, depicted schematically in FIG. 2, containing an internal dR-Biotin can be cut by Nfo and fpg. The reactions (total volume of 150 µL) were mixed from fresh reagents and incubated for 75 minutes at 37° C. Conditions used were 50 mM Tris/Acetate (pH 7.9), 14 mM Mg-Acetate, 100 mM Potassium-Acetate, 2 mM DTT, 200 nM each dNTP, 6% PEG 35,000, 3 mM ATP, 50 mM Phospho-Creatine, 900 ng/µL T4gp32, 120 ng/µL, T4uvsX, 30 ng/µL T4uvsY, 360 ng/µL *Bac. subtilis* DNA polI. Either 3000 copies of DNA template or water (as a negative control) was included as indicated. Nuclease, 200 ng/µL Nfo or 50 ng/µL fpg, was included as indicated. Primers, K2 and J1, were included at 480 nM each and the probe, FpgProb1, was included at 120 nM, with their sequences provided below. Samples were quenched in one volume of 2% SDS/one volume phenol, mixed and incubated for 20 minutes at 65° C. Subsequently samples were phenol/chloroform extracted and twice ethanol precipitated according to standard molecular biology techniques. Half of each sample was then resuspended in formamide loading buffer resolved on a 16.5% denaturing polyacrylamide gel (Urea) and visualised (using the FAM fluorescence) following standard protocols. Markers were 2 pmol of the probe and 2 pmol of a 32 nt marker oligonucleotide.

```
J1
                                           (SEQ ID NO: 1)
5'-acggcattaacaaacgaactgattcatctgcttgg-3'

K2
                                           (SEQ ID NO: 2)
5'-ccttaatttctccgagaacttcatattcaagcgtc-3'

FpgProbe1
                                           (SEQ ID NO: 3)
5'-6FAM-cagaagtatgaccgtgtctttgaaatg[dR-biotin]
ttgaagaaatggtt[ddC]-3'
```

The probe and any derivatives were visualised here by virtue of the FAM moiety which emits visible light when excited by UV radiation. Amplification reactions (RPA) containing a target DNA, two (2) appropriate amplification primers, the dR-biotin probe and either no nuclease, Nfo protein, or fpg protein were cleaned following incubation and separated by size on a denaturing acrylamide gel and then exposed to UV. The probe or any derivatives retaining the 5'-FAM are then visible (FIG. 3). In the absence of an added nuclease, the probe, 42 nucleotides long, mostly migrates at its expected location slightly more slowly than a control labelled primer of 32 nucleotides (indicated). A slightly slower-migrating (longer) fragment is also seen as compared to the neat probe not incubated in RPA (#1). This likely arose because the probe can be unblocked slowly by nucleases that are believed to be present in some of the enzyme preparations (nibbling at the 3' end), and once unblocked it can be extended following hybridization to amplifying target and hence forming a nested amplicon of sorts. In the presence of Nfo however, this phenomenon is much more prominent as expected and a large proportion of the probe is now elongated. Furthermore, the Nfo protein was indeed attacking the dR-O—[C]n residue rather than just 'polishing' the 3' end because some small amount of faster-migrating probe DNA (#2) is also visible indicating cleavage at the dR-O—[C]n location with no subsequent elongation. Finally, when fpg protein was included in the reaction environment a large proportion of faster-migrating cleaved probe is visible and no elongated material is detected, as fpg leaves a blocked 3'-end after cleavage and hence it is not extended by polymerase enzyme present in the mix.

Example 2

Measurement of DNA Amplification with Oligonucleotides Probes Containing an Internal dR-Fluorophore In this Example, RPA experiments using fluorescent reagents in which the dR-O—[C]n nucleotide is coupled to a fluorophore as depicted in FIG. 4. In this case, the dR-fluorophore is positioned close to the 5' end of the oligonucleotide probe and in close proximity to a quencher which is attached to the very 5' end. As in the previous example, the 3' end of the probe is suitably blocked to prevent aberrant elongation or primer artefacts.

The reactions (total volume of 50 µL) were performed according to standard RPA protocol for freeze-dried reactions. Briefly, lyophilised reagents were mixed with PEG, Magnesium-Acetate and template, and incubated for 20 minutes at 38° C. in a fluorometer (Twista prototype; ESE GmbH, Germany). Conditions used were 50 mM Tris/Acetate (pH 8.3), 14 mM Mg-Acetate, 100 mM Potassium-Acetate, 5 mM DTT, 240 nM each dNTP, 5% PEG 35,000, 4% Trehalose 2.5 mM ATP, 50 mM Phospho-Creatine, 300 ng/µL rb69gp32, 273 ng/µL uvsX, 120 ng/µL uvsY, 50 ng/µL *Staph. aureus* DNA polI. For the experiments of FIG. 5, 1000, 100, 10 or 0 copies of the DNA template was included as indicated in the figure, while 1000 copies of the DNA template was included for the experiments of FIG. 6. Fpg nuclease, 25 ng/µL, was included. Primers were included at 360 nM each and probe was included at 120 nM, with their sequences provided below. Fluorescence was measured every 20 seconds (excitation 470 nM, emission 520 nM). Samples were removed from the incubator for a brief mix/spin at 4 minutes of incubation time and returned to the incubator/fluorometer. Arbitrary fluorescence units were plotted against time in minutes.

For human genomic locus rs4824871 the sequences of the primers, F2 and R1, and the probe used were:

F2
(SEQ ID NO: 4)
5'-ccatcctcaatactaagctaagtaaaaagattt-3'

R1
(SEQ ID NO: 5)
5'-ccctgtggctaagagctcttgatagtcaaagta-3'

Probe
(SEQ ID NO: 6)
BHQ1-5'-cctt[dR-FAM]tctaaggaaatggacag
aaataggcaagat[ddC]-3'

For human genomic locus rs1207445 the sequences of the primers, F2 and R2, and the probe used were:

F2
(SEQ ID NO: 7)
5'-cccttctgatattctaccaaatgccccctaaat-3'

R2
(SEQ ID NO: 8)
5'-catgtgtataagaaaactacccaagcctaggga-3'

Probe
(SEQ ID NO: 9)
BHQ1-5'-cagtg[dR-FAM]ccaatacacacac
aagactgggcatgg[ddC]-3'

For human genomic locus rs1105561 the sequences of the primers, F1 and R1, and the probe used were:

F1
(SEQ ID NO: 10)
5'-tatagtggaaaggtgttcatttgtataaacccc-3'

R1
(SEQ ID NO: 11)
5'-cacataaatcagagaatgtgtgtggggtcatgtat-3'

Probe
(SEQ ID NO: 12)
BHQ1-5'-aactt[dR-FAM]gcaactaacgctaaa
ttataatcacttct[ddC]-3'

For human genomic locus rs5923931 the sequences of the primers, F1 and R1, and the probe used were:

F1
(SEQ ID NO: 13)
5'-catttctcaaaagaagatatgcaaataaaaca-3'

R1
(SEQ ID NO: 14)
5'-ccattataactggggtgagatgatatctcattg-3'

Probe
(SEQ ID NO: 15)
BHQ1-5'-tctca[dR-FAM]cataactgatcatcag
agaaatgtaaatc[ddC]-3'

FIGS. 5 and 6 show the outcome of the above experiments in which RPA reactions were performed on human genomic targets utilizing primers and probes specifically directed toward known SNP regions. In FIG. 5 two such genomic regions were amplified using RPA and probes with the general structure depicted in FIG. 4, along with the inclusion of the fpg protein. Target genomic DNA has been added to give a total target copy number of 1000, 100, 10 or zero target molecules, and in this way the requirement for the specific accumulation of amplicons matching the target is ensured. Note that after between 6 and 12 minutes (depending on the target and copy number) there is a clear rise in fluorescence in those samples containing target, whilst those lacking targets remain with more-or-less stable fluorescence. In FIG. 6 there is similar data shown for four human genomic DNA target/probe sets (two of which were also used in FIG. 5) and in each case fluorescence rises at about the expected time of DNA amplification. In addition to these and other successful probes, we have encountered occasional probes that did not seem to work well in RPA amplification/detection systems (maybe 10-20% of those analyzed) however the source of these failures is as yet unclear, potentially reflecting failures in RPA amplification in some cases rather than probe failure, potentially as a result of probe failure in other cases. We speculate that in some cases the position and nature of adjacent bases, or the nature of the base opposing the dR-O—[C]n group could play a part in the effectiveness of the probe.

Although particular embodiments have been disclosed herein in detail, this has been done by way of example for purposes of illustration only, and is not intended to be limiting with respect to the scope of the appended claims, which follow. In particular, it is contemplated by the inventors that various substitutions, alterations, and modifications may be made to the invention without departing from the spirit and scope of the invention as defined by the claims. Other aspects, advantages, and modifications considered to be within the scope of the following claims. The claims presented are representative of the inventions disclosed herein. Other, unclaimed inventions are also contemplated. Applicants reserve the right to pursue such inventions in later claims.

We claim:

1. An oligonucleotide having a first 5'-end and a first extension blocked 3'-end, the oligonucleotide comprising:
    a dR-O—[C]n nucleotide that lacks a base and has a sugar with a carbon at a 1' position, and wherein the carbon at the 1' position is covalently linked through an oxygen atom to a carbon atom of a linker containing n carbon atoms, wherein said oligonucleotide contains a fluorophore-quencher pair separated by 10 nucleotides or less,
    wherein the dR-O—[C]n nucleotide is conjugated with either the fluorophore or the quencher,
    wherein the oligonucleotide is between 30 and 60 nucleotides in length,
    wherein cleavage of the oligonucleotide by 8-oxoguanine DNA glycosylase yields (i) a first fragment comprising the first 5'-end and a second extension blocked 3'-end and (ii) a second fragment comprising a second 5'-end and the first extension blocked 3'-end, and
    wherein n is 1-8.

2. The probe of claim 1, wherein n is 3-6.

3. The probe of claim 2, wherein n is 6.

4. The probe of claim 1, wherein the fluorophore and quencher are separated by 4-6 bases.

5. The probe of claim 1, wherein the fluorophore or quencher not conjugated to the dR-O—[C]n nucleotide is conjugated at one end of the probe.

6. The probe of claim 5, wherein the conjugated end of the probe is the 5'-end.

7. A kit, comprising
    (i) an oligonucleotide having a first 5'-end and a first extension blocked 3'-end, the oligonucleotide comprising a dR-O—[C]n nucleotide that lacks a base and has a sugar with a carbon at a 1' position, and wherein the carbon at the 1' position is covalently linked through an oxygen atom to a carbon atom of a linker containing n carbon atoms,
    wherein the dR-O—[C]n nucleotide is conjugated with either the fluorophore or the quencher,
    wherein the oligonucleotide is between 30 and 60 nucleotides in length,
    wherein cleavage of the oligonucleotide by 8-oxoguanine DNA glycosylase yields (i) a first fragment comprising the first 5'-end and a second extension blocked 3'-end and (ii) a second fragment comprising a second 5'-end and the first extension blocked 3'-end, and
    wherein n is 1-8; and
    (ii) 8 oxoguanine DNA glycosylase (fpg).

8. The kit of claim 7, wherein n is 3-6.

9. The kit of claim 7, wherein n is 6.

10. A reaction mixture comprising
    an oligonucleotide having a first 5'-end and a first extension blocked 3'-end, the oligonucleotide comprising a dR-O—[C]n nucleotide that lacks a base and has a sugar with a carbon at a 1' position, and wherein the carbon at the 1' position is covalently linked through an oxygen atom to a carbon atom of a linker containing n carbon atoms,
    wherein the dR-O—[C]n nucleotide is conjugated with either the fluorophore or the quencher,
    wherein the oligonucleotide is between 30 and 60 nucleotides in length,
    wherein cleavage of the oligonucleotide by 8-oxoguanine DNA glycosylase yields (i) a first fragment comprising the first 5'-end and a second extension blocked 3'-end and (ii) a second fragment comprising a second 5'-end and the first extension blocked 3'-end, and
    wherein n is 1-8; and
    8-oxoguanine DNA glycosylase (fpg).

11. The reaction mixture of claim 10 wherein n is 3-6.

12. The reaction mixture of claim 11, wherein n is 6.

13. The reaction mixture of claim 10, wherein the reaction mixture is lyophilized.

14. The reaction mixture of claim 10, further comprising a container.

15. The reaction mixture according to claim 14, wherein the container is a tube.

16. The reaction mixture of claim 10, further comprising a target nucleic acid that contains a sequence complementary to the oligonucleotide.

* * * * *